(12) United States Patent
Addis et al.

(10) Patent No.: US 7,279,001 B2
(45) Date of Patent: Oct. 9, 2007

(54) SYSTEMS, METHODS, AND COMPOSITIONS FOR ACHIEVING CLOSURE OF VASCULAR PUNCTURE SITES

(75) Inventors: Bruce Addis, Redwood City, CA (US); Charles Milo, Mountain View, CA (US); Olexander Hnojewyj, Saratoga, CA (US)

(73) Assignee: NeoMend, Inc., Irvine, CA (US)

( * ) Notice: Subject to any disclaimer, the term of this patent is extended or adjusted under 35 U.S.C. 154(b) by 55 days.

(21) Appl. No.: 10/141,510

(22) Filed: May 8, 2002

(65) Prior Publication Data

US 2003/0100921 A1 May 29, 2003

Related U.S. Application Data

(63) Continuation-in-part of application No. 09/780,843, filed on Feb. 9, 2001, now Pat. No. 6,949,114, which is a continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(51) Int. Cl.
*A61B 17/08* (2006.01)
*A61D 1/00* (2006.01)

(52) U.S. Cl. ........................ 606/214; 606/213
(58) Field of Classification Search ........ 606/213–215; 604/181, 183, 184, 191, 57, 58, 148, 15, 604/82
See application file for complete search history.

(56) References Cited

U.S. PATENT DOCUMENTS

| | | | |
|---|---|---|---|
| 4,101,380 A | | 7/1978 | Rubinstein et al. |
| 4,161,948 A | | 7/1979 | Bichon |
| 4,414,976 A | * | 11/1983 | Schwarz et al. ............ 606/214 |
| 4,464,468 A | | 8/1984 | Avrameas et al. |
| 4,762,129 A | | 8/1988 | Bonzel |
| 4,839,345 A | | 6/1989 | Doi et al. |
| 4,909,251 A | * | 3/1990 | Seelich ....................... 606/213 |
| 4,929,246 A | | 5/1990 | Sinofsky |

(Continued)

FOREIGN PATENT DOCUMENTS

WO WO96/11671 4/1996

(Continued)

OTHER PUBLICATIONS

Transactors: Society for Biomaterials: Protoelytically Degradable Hydrogels; West et al (1997).

*Primary Examiner*—Michael J. Hayes
*Assistant Examiner*—Michael G. Mendoza
(74) *Attorney, Agent, or Firm*—Ryan Kromholz & Manion, S.C.

(57) ABSTRACT

Systems and methods convey a closure material into a catheter, e.g., to seal a puncture site in a blood vessel. The closure material comprises a mixture of first and second components, which, upon mixing, undergo a reaction to form solid closure material composition. The first component may be a lyophilized polyethylene glycol (PEG) material contained within a vial. The second component may be a buffered albumin solution plus water contained within a syringe. An applicator provides easy and effective mixing of the components and delivery of the mixture to the puncture site.

1 Claim, 15 Drawing Sheets

U.S. PATENT DOCUMENTS

| | | |
|---|---|---|
| 5,051,406 A | 9/1991 | Satoh |
| 5,129,882 A | 7/1992 | Weldon et al. |
| 5,207,670 A | 5/1993 | Sinofsky |
| 5,252,714 A | 10/1993 | Harris et al. |
| 5,318,524 A | 6/1994 | Morse et al. |
| 5,383,896 A | 1/1995 | Gershony et al. |
| 5,403,278 A | 4/1995 | Ernst et al. |
| 5,410,016 A | 4/1995 | Hubbell et al. |
| 5,419,765 A | 5/1995 | Weldon et al. |
| 5,514,379 A | 5/1996 | Weissleder et al. |
| 5,520,885 A | 5/1996 | Coelho et al. |
| 5,529,577 A | 6/1996 | Hammerslag |
| 5,529,915 A * | 6/1996 | Phillips et al. ............... 435/188 |
| 5,531,683 A * | 7/1996 | Kriesel et al. ................. 604/89 |
| 5,567,435 A | 10/1996 | Hubbell et al. |
| 5,582,596 A | 12/1996 | Fukunaga et al. |
| 5,583,114 A | 12/1996 | Barrows et al. |
| 5,601,602 A | 2/1997 | Fowler |
| 5,626,601 A | 5/1997 | Gershony et al. |
| 5,626,863 A | 5/1997 | Hubbell et al. |
| 5,649,959 A | 7/1997 | Hannam et al. |
| 5,653,730 A | 8/1997 | Hammerslag |
| 5,672,662 A | 9/1997 | Harris et al. |
| 5,676,689 A | 10/1997 | Kensey et al. |
| 5,725,498 A | 3/1998 | Janzen et al. |
| 5,733,563 A | 3/1998 | Fortier |
| 5,739,208 A | 4/1998 | Harris |
| 5,746,755 A | 5/1998 | Wood et al. |
| 5,749,968 A * | 5/1998 | Melanson et al. .......... 118/300 |
| 5,759,169 A | 6/1998 | Marx |
| 5,759,194 A | 6/1998 | Hammerslag |
| 5,782,860 A | 7/1998 | Epstein et al. |
| 5,791,352 A | 8/1998 | Reich et al. |
| 5,814,022 A * | 9/1998 | Antanavich et al. ........ 604/191 |
| 5,824,015 A | 10/1998 | Sawyer |
| 5,843,124 A | 12/1998 | Hammerslag |
| 5,844,016 A | 12/1998 | Sawhney et al. |
| 5,858,746 A | 1/1999 | Hubbell et al. |
| 5,874,500 A | 2/1999 | Rhee et al. |
| 5,900,245 A | 5/1999 | Sawhney et al. |
| 5,900,461 A | 5/1999 | Harris |
| 5,922,009 A | 7/1999 | Epstein et al. |
| 5,932,462 A | 8/1999 | Harris et al. |
| 5,935,147 A | 8/1999 | Kensey et al. |
| 5,935,437 A | 8/1999 | Whitmore |
| 5,936,035 A | 8/1999 | Rhee et al. |
| 5,942,209 A | 8/1999 | Leavitt et al. |
| 5,951,160 A * | 9/1999 | Ronk .......................... 366/130 |
| 5,951,583 A | 9/1999 | Jensen et al. |
| 5,951,589 A | 9/1999 | Epstein et al. |
| 5,986,043 A | 11/1999 | Hubbell et al. |
| 5,990,237 A | 11/1999 | Bentley et al. |
| 6,007,613 A | 12/1999 | Izoret |
| 6,022,336 A | 2/2000 | Zadno-Azizi et al. |
| 6,022,361 A | 2/2000 | Epstein et al. |
| 6,051,248 A | 4/2000 | Sawhney et al. |
| 6,060,582 A | 5/2000 | Hubbell et al. |
| 6,083,524 A | 7/2000 | Sawhney et al. |
| 6,152,943 A | 11/2000 | Sawhney |
| 6,162,241 A | 12/2000 | Coury et al. |
| 6,165,201 A | 12/2000 | Sawhney et al. |
| 6,177,095 B1 | 1/2001 | Sawhney et al. |
| 6,179,862 B1 | 1/2001 | Sawhney |
| 6,183,498 B1 * | 2/2001 | Devore et al. .............. 606/214 |
| 6,371,975 B2 | 4/2002 | Cruise et al. |
| 6,379,373 B1 | 4/2002 | Sawhney et al. |
| 6,458,889 B1 * | 10/2002 | Trollsas et al. ............ 525/54.1 |
| 6,475,182 B1 | 11/2002 | Hnojewyj et al. |
| 6,478,771 B1 * | 11/2002 | Lavi et al. .................... 604/82 |
| 6,818,018 B1 | 11/2004 | Sawhney |

FOREIGN PATENT DOCUMENTS

| | | |
|---|---|---|
| WO | WO97/22371 | 6/1997 |
| WO | WO99/07417 | 2/1999 |
| WO | WO99/14259 | 3/1999 |
| WO | WO99/45964 | 9/1999 |
| WO | WO 00/09087 | 2/2000 |
| WO | WO 00/09199 | 2/2000 |
| WO | WO 00/33764 | 6/2000 |

* cited by examiner

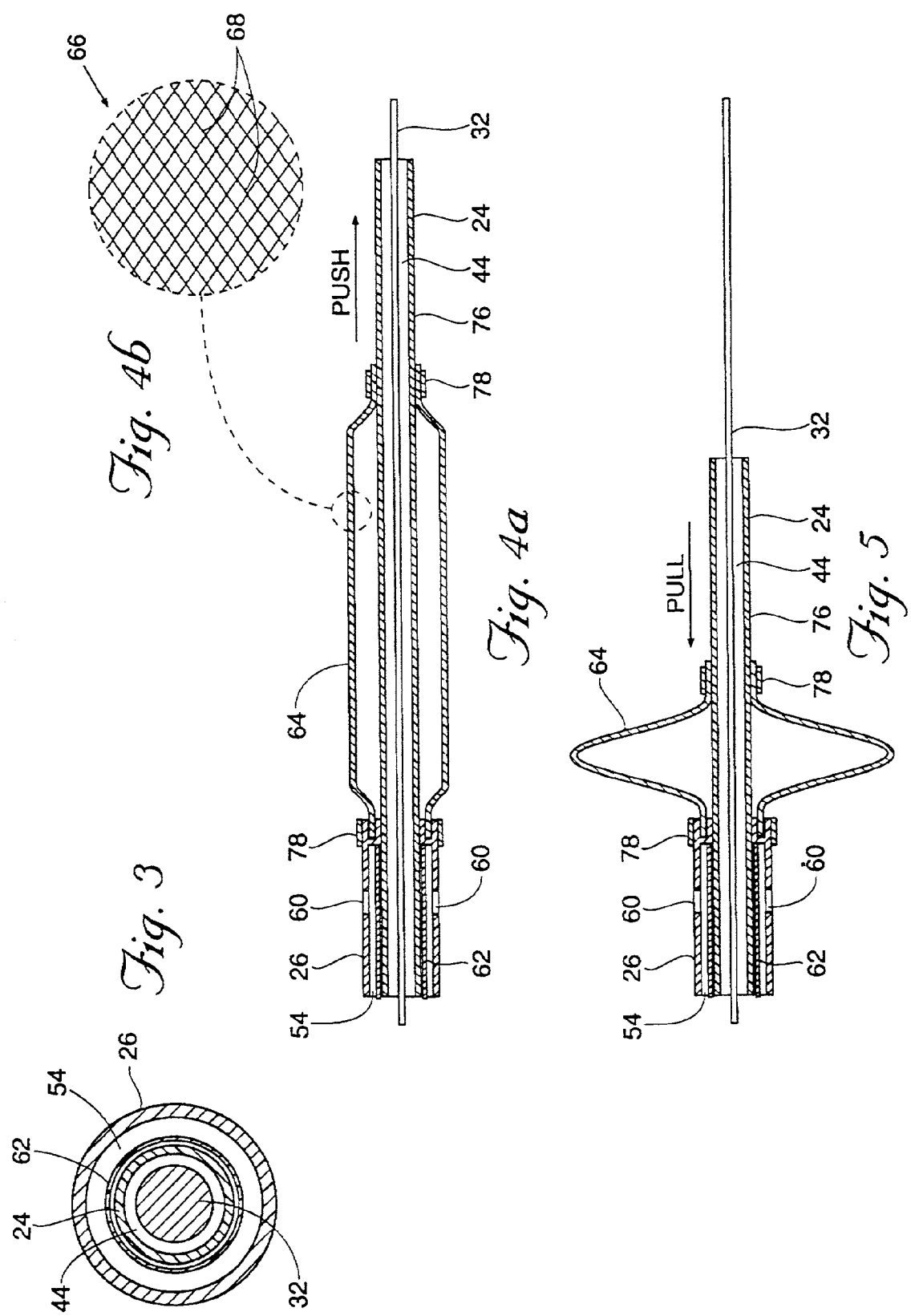

SYSTEMS, METHODS, AND COMPOSITIONS FOR ACHIEVING CLOSURE OF VASCULAR PUNCTURE SITES

RELATED APPLICATIONS

This application is a continuation-in-part of U.S. patent application Ser. No. 09/780,843, filed Feb. 9, 2001 now U.S. Pat. No. 6,949,114, and entitled "Systems, Methods, and Compositions for Achieving Closure of Vascular Puncture Sites," which is a continuation-in-part of U.S. patent application Ser. No. 09/283,535, filed Apr. 1, 1999 now U.S. Pat. No. 6,458,147, and entitled "Compositions, Systems, And Methods For Arresting or Controlling Bleeding or Fluid Leakage in Body Tissue," which is itself a continuation-in-part of U.S. patent application Ser. No. 09/188,083, filed Nov. 6, 1998 now U.S. Pat. No. 6,371,975, and entitled "Compositions, Systems, and Methods for Creating in Situ, Chemically Cross-linked, Mechanical Barriers."

FIELD OF THE INVENTION

The invention generally relates to the systems and methods for delivering biocompatible materials to body tissue to affect desired therapeutic results.

BACKGROUND OF THE INVENTION

There are many therapeutic indications today that pose problems in terms of technique, cost efficiency, or efficacy, or combinations thereof.

For example, following an interventional procedure, such as angioplasty or stent placement, a 5 Fr to 9 Fr arteriotomy remains. Typically, the bleeding from the arteriotomy is controlled through pressure applied by hand, by sandbag, or by C-clamp for at least 30 minutes. While pressure will ultimately achieve hemostasis, the excessive use and cost of health care personnel is incongruent with managed care goals.

Various alternative methods for sealing a vascular puncture site have been tried. For example, collagen plugs have been used to occlude the puncture orifice. The collagen plugs are intended to activate platelets and accelerate the natural healing process. Holding the collagen seals in place using an anchor located inside the artery has also been tried. Still, patient immobilization is required until clot formation stabilizes the site. Other problems, such as distal embolization of the collagen, rebleeding, and the need for external pressure to achieve hemostasis, also persist.

As another example, devices that surgically suture the puncture site percutaneously have also been used. The devices require the practice of fine surgical skills to place needles at a precise distance from the edges of the puncture orifice and to form an array of suture knots, which are tightened and pushed from the skin surface to the artery wall with a knot pusher, resulting in puncture edge apposition.

There remains a need for fast and straightforward mechanical and chemical systems and methods to close vascular puncture sites and to accelerate the patient's return to ambulatory status without pain and prolonged immobilization.

There also remains a demand for biomaterials that improve the technique, cost efficiency, and efficacy of these and other therapeutic indications.

SUMMARY OF THE INVENTION

One aspect of the invention provides systems and methods for mixing and dispensing materials. The systems and methods provide an applicator that serves to couple a dispenser to a container. The dispenser holds a first material. The container holds a second material, which is intended to be mixed with the first material and conveyed in mixed form to a targeted delivery site. The dispenser has an actuator that can be operated by a user. Once the dispenser is coupled by the applicator to the container, operation of the actuator can perform two, essentially concurrent functions: (i) it can dispense the first material from the dispenser into the container, where it mixes with second material, and (ii) upon continued operation of the actuator, it can convey the mixture from the container for delivery to an external targeted site. The applicator makes it possible to combine, by the straightforward operation of a single actuator, the essentially concurrent mixing and delivery of two materials.

Another aspect of the invention provides an assembly comprising a biocompatible polymer comprising poly(ethylene glycol) (PEG) with a functionality of at least three. According to this aspect of this aspect of the invention, the polymer is in lyophilized form. A container holds the polymer in lyophilized form prior to use.

Another aspect of the invention provides systems and methods for dispensing a polymer that is moisture sensitive. The systems and methods dissolve the polymer in an aqueous solution to form a dissolved polymer solution. The systems and methods lyophilize the dissolved polymer solution to form a lyophilized polymer. The systems and methods reconstitute the lyophilized polymer mixture with an aqueous solution to form a reconstituted polymer solution. The systems and methods dispense the reconstituted polymer solution. In one embodiment, the systems and methods store the lyophilized polymer mixture in an inert atmosphere.

DESCRIPTION OF THE DRAWINGS

FIG. 3 is a cross section view of the inner and outer catheter bodies that comprise the catheter assembly shown in FIG. 2, taken generally along section line 3-3 in FIG. 2.

FIG. 4A is an enlarged section view of the distal end of a catheter assembly that forms a part of the vascular puncture site access assembly shown in FIG. 1, showing the expandable structure carried by the assembly in a collapsed condition.

FIG. 4B is an enlarged view of the wall of the expandable structure shown in FIG. 4A, showing its open or woven configuration that allows blood flow through the structure.

FIG. 5 is an enlarged section view of the distal end of a catheter assembly that forms a part of the vascular puncture site access assembly shown in FIG. 1, showing the expandable structure carried by the assembly in an expanded condition.

FIGS. 11-16 illustrate the use of the formative component assembly to deliver a closure composition to a vascular puncture site, wherein

FIG. 12 is a perspective view illustrating the insertion of the syringe component of the formative component assembly shown in FIG. 1 into to the applicator component;

FIG. 13 is a perspective view illustrating the procedure of coupling the assembled formative component assembly shown in FIG. 8 to the introducer/mixer assembly, which is coupled to the catheter assembly as shown in FIG. 10;

FIG. 14 is a perspective view illustrating the advancement of the syringe plunger component of the formative component assembly and further illustrating the transfer of the liquid component in the syringe into the vial containing the solid component mixture of the liquid and the reconstituted solid components in the vial;

FIG. 15 is a perspective view illustrating the urging of the mixture from the vial through the second needle component of the formative component assembly and into the introducer/mixer assembly;

FIG. 16 is a perspective view illustrating the syringe and vial after the mixture has been transferred from the vial to the introducer/mixer assembly, and further illustrating residual mixture in the vial;

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

The systems and methods disclosed herein are shown in the particular context of closing a vascular puncture site. That is because the systems and methods are well suited for use in this indication, and this indication thus provides a representative embodiment for purposes of description. Still, it should be appreciated that the systems and methods described can, with appropriate modification (if necessary), be used for diverse other indications as well, and in conjunction with delivery mechanisms that are not necessarily catheter-based. For example, the systems and methods can be used with delivery mechanisms which spray materials, e.g., for the purpose of tissue sealing or adhesion prevention. As another example, the systems and methods can be used with delivery mechanisms which use cannulas, e.g., for the purpose of filling tissue voids or aneurysms, or for tissue augmentation. As yet another example, the systems and methods can be used to deliver drug or cells to targeted locations.

System Overview

Figure 1:
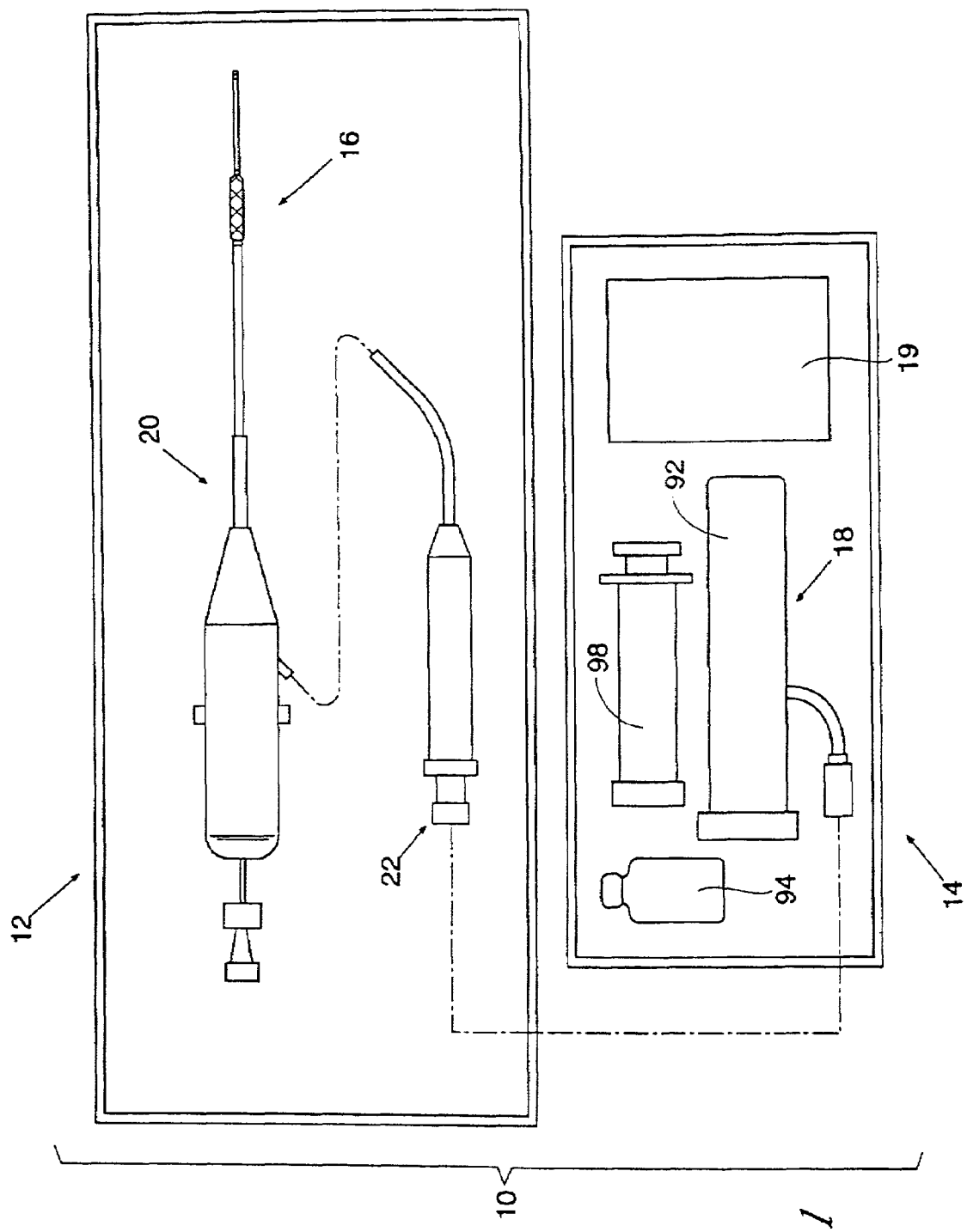
FIG. 1 is a view of a system of functional instruments for closure of a vascular puncture site e.g., following a vascular access procedure, comprising a vascular puncture site access assembly, to gain transcutaneous access to the vascular puncture site for the purpose of delivering a biocompatible material closure composition, and a formative component assembly, to house the components of the biocompatible material closure composition prior to use.

FIG. 1 shows a system 10 of functional instruments for closure of a vascular puncture site e.g., following a vascular access procedure.

As will be described in greater detail, the instruments of the system 10 are, during use, deployed in a purposeful manner to gain transcutaneous access to a vascular puncture site. The instruments of the system 10 are manipulated to place a biocompatible material composition outside the blood vessel at the puncture site. The biocompatible material composition produces a solid, three dimensional matrix that closes the puncture site.

In a preferred embodiment, the biocompatible material composition is comprised of two or more formative components which are mixed in a liquid state while being delivered by the system 10 transcutaneously to the puncture site. Upon mixing, the formative components react, in a process called "gelation," to transform in situ from the liquid state, to a semi-solid (gel) state, and then to the biocompatible solid state.

In the solid state, the composition takes the form of a non-liquid, three-dimensional network. Desirably, the solid material composition exhibits adhesive strength (adhering it to adjacent tissue), cohesive strength (forming a mechanical barrier that is resistant to blood pressure and blood seepage), and elasticity (accommodating the normal stresses and strains of everyday activity). These properties provide an effective closure to the vascular puncture site.

The solid material composition is also capable of transforming over time by physiological mechanisms from the solid state to a biocompatible liquid state, which can be cleared by the body, in a process called "degradation."

As FIG. 1 shows, in one embodiment, the system 10 can be contained, prior to use, in two functional kits 12 and 14.

The first kit 12 contains a vascular puncture site access assembly 16. The purpose of the access assembly 16 is to gain transcutaneous access to the vascular puncture site for the purpose of delivering the biocompatible material composition.

The second kit 14 contains a formative component assembly 18 and directions for use 19. The purpose of the formative component assembly 18 is to house the components of the biocompatible material composition prior to use. As will be described in greater detail later, these components are mixed and delivered by the access assembly 16 to the puncture site. The directions for use 19 provide the user with a step-by-step procedure and information for use of the assembly 18, as will be described in greater detail later (see FIGS. 11-16).

The kits 12 and 14 can take various forms. In the illustrated embodiment, each kit 12 and 14 comprises a sterile (e.g., sterilized by ethylene oxide gas), wrapped assembly.

The Access Assembly

As FIG. 1 shows, the access assembly 16 comprises a catheter assembly 20 and a component introducer/mixer assembly 22.

The Catheter Assembly

The catheter assembly comprises a flexible inner catheter body 24 that is slidably carried within a flexible outer catheter body 24 (see FIGS. 2 to 5). The inner and outer catheter bodies 24 and 26 can be made from an extruded plastic material, e.g., PEBAX™ material. The outside diameter of the outer catheter body 26 can vary, e.g., from 6 Fr. to 10 Fr.

Figure 17:
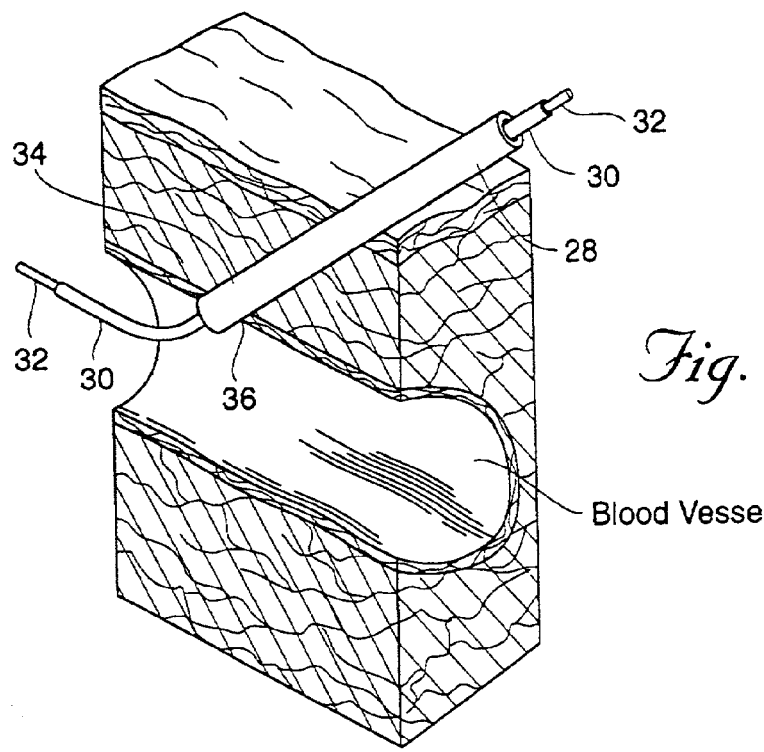
FIG. 17 is a diagrammatic view of blood vessel puncture site formed to enable the delivery of a diagnostic or therapeutic instrument through a vascular sheath and over a guide wire.
Figure 18:
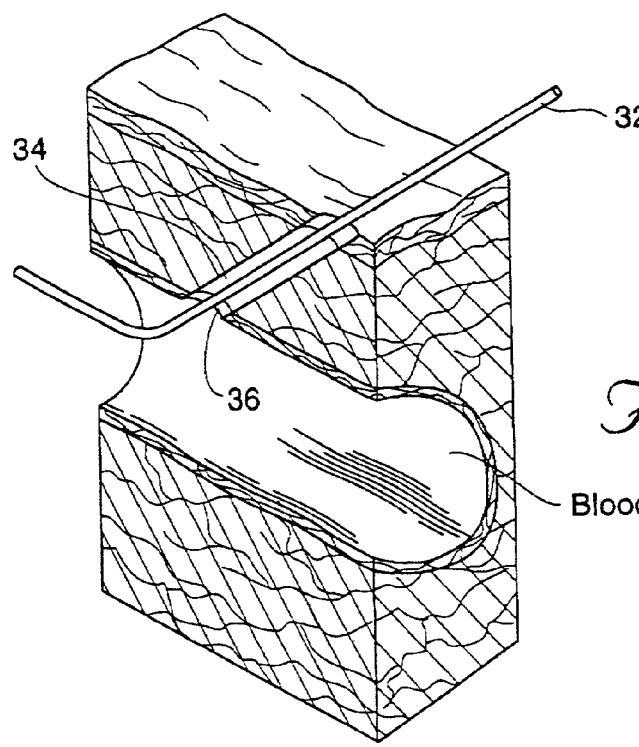
FIG. 18 is a diagrammatic view of the blood vessel puncture site shown in FIG. 17, after removal of the diagnostic or therapeutic instrument and vascular sheath, keeping the guide wire deployed.
Figure 19:
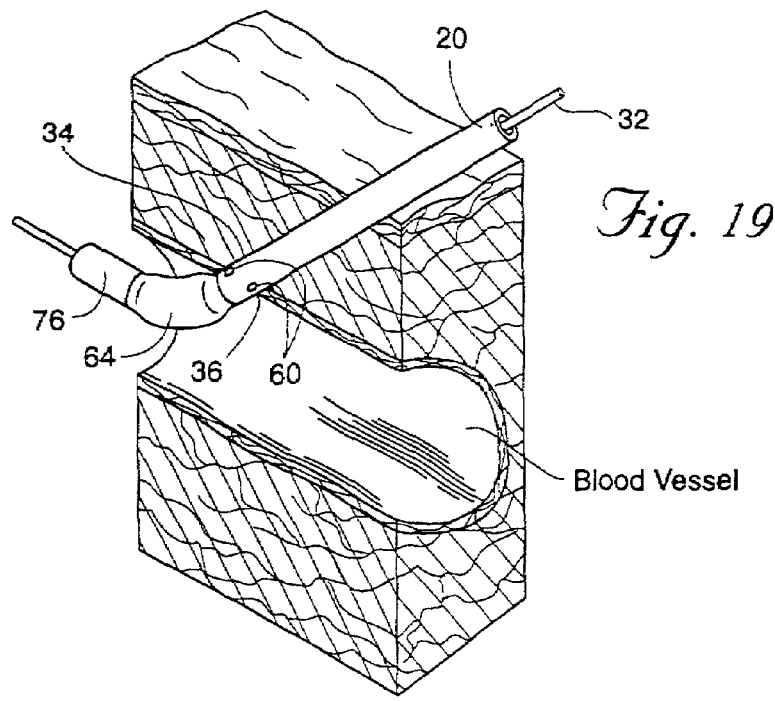
FIG. 19 is a diagrammatic view of the blood vessel puncture site shown in FIG. 18, during deployment of the vascular puncture site access assembly shown in FIG. 1, the access assembly being deployed over the guide wire with the expandable structure in a collapsed condition.
Figure 20:
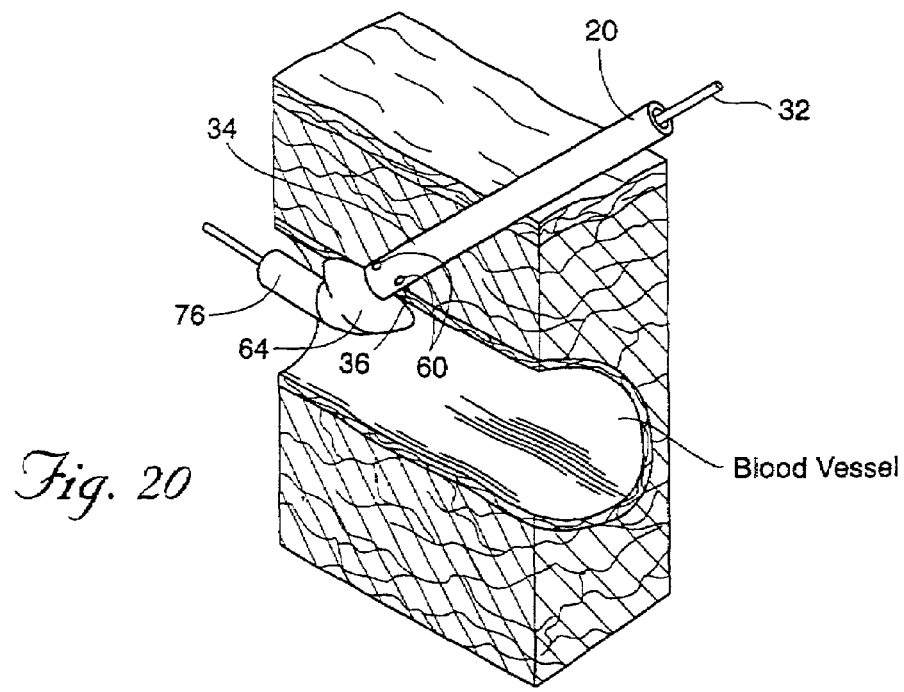
FIG. 20 is a diagrammatic view of the blood vessel puncture site shown in FIG. 19, with the vascular puncture site access assembly deployed and the expandable structure in an expanded condition serving as a positioner within the blood vessel for the closure composition delivery nozzles outside the blood vessel.
Figure 21:
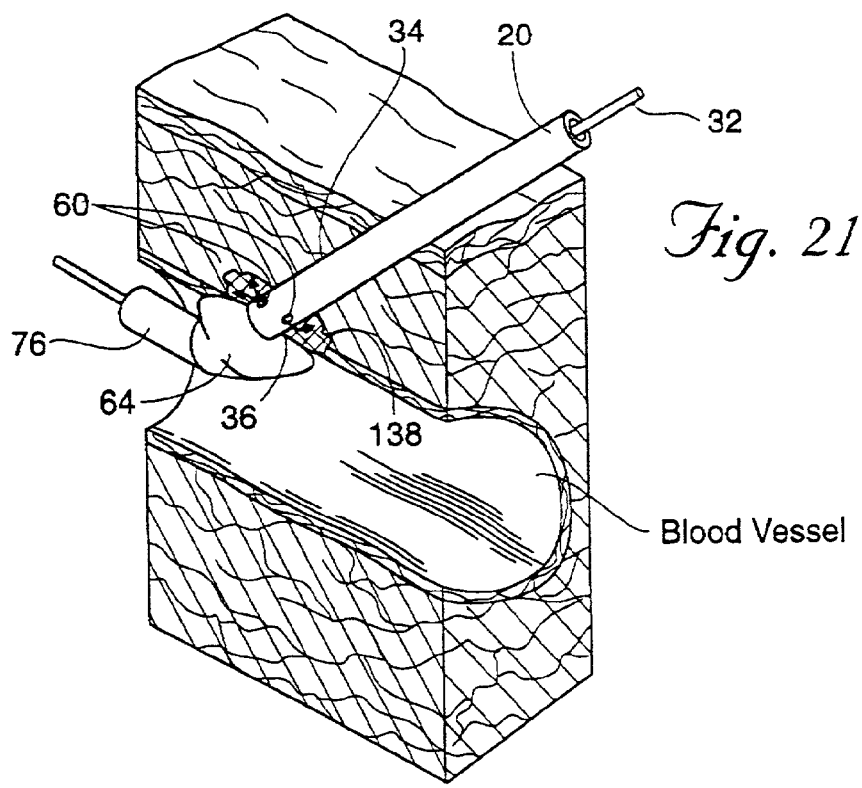
FIG. 21 is a diagrammatic view of the blood vessel puncture site shown in FIG. 20, as the closure composition is being delivered through the closure composition delivery nozzles outside the blood vessel.

The outside diameter of the outer catheter body 26 is sized to seal the tissue track 34 through which it is introduced, so that its presence is hemostatic (see FIGS. 19-21). The tissue track 34 typically will have been previously formed by a vascular introducer or cannula 28 (see FIG. 17), through which the desired therapeutic or diagnostic instrument is first introduced (typically over a guide wire 32) through a puncture site 36 into the vessel, e.g., to perform coronary angioplasty. After performing the intended procedure, the instrument 30 and introducer 28 are withdrawn (see FIG. 18), leaving the puncture site 36 and the tissue track 34. The outside diameter of the outer catheter body 26 is selected to match the outside diameter of the vascular introducer 28, so that the outer catheter body 26, when deployed, will block substantial flow of blood from the puncture site 36 up the tissue track 34.

Figure 2:
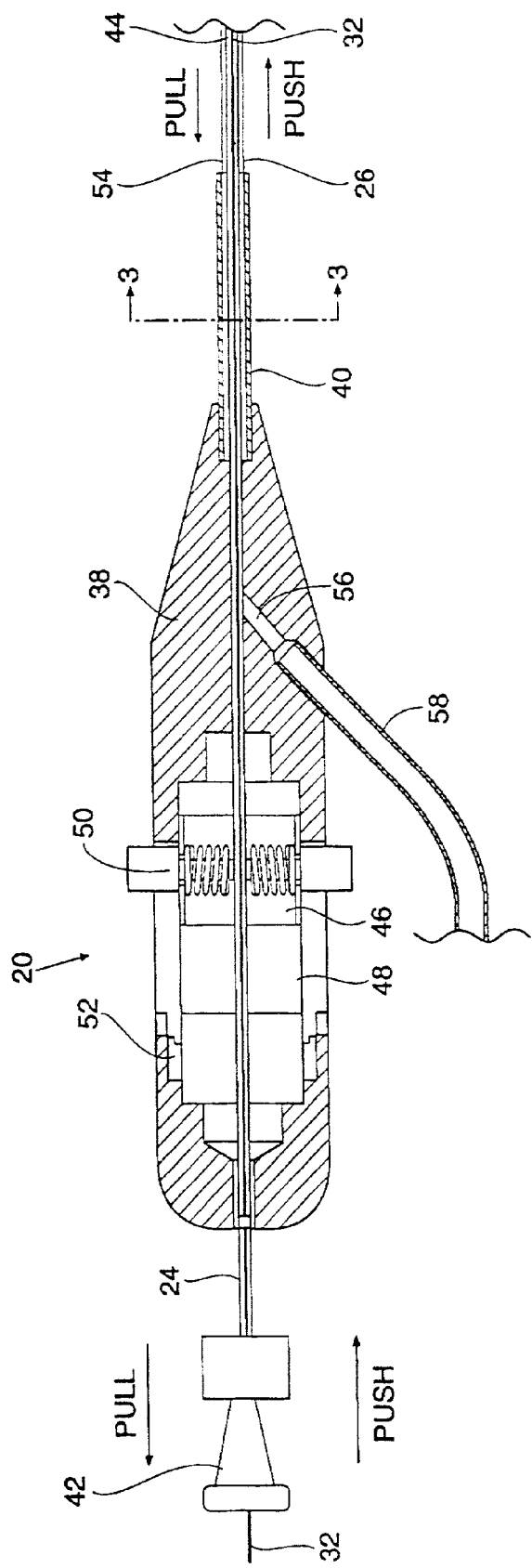
FIG. 2 is an enlarged section view of the proximal end of a catheter assembly that forms a part of the vascular puncture site access assembly shown in FIG. 1.

The proximal end of the outer catheter body 26 is secured, e.g., by adhesive, to the distal end of a preformed y-shaped adapter 38 (see FIG. 2). The adapter 38 serves as a handle for the entire catheter assembly 20. A strain relief sheath 40 desirably encompasses the outer catheter body 26 adjacent the handle 38.

The proximal end of the inner catheter body 24 extends through and beyond the handle 38. The exposed end of the inner catheter body 24 desirably carries a luer fitting 42, so that a flushing fluid can be introduced through the inner catheter body 24. The inside diameter of the inner catheter body 24 defines an interior lumen 44 (see FIG. 3) that is sized to accommodate passage of the guide wire 32.

A carrier 46 is carried on a track 48 in the handle 38 for fore and aft sliding movement. The inner catheter body 24 is adhesively secured within the sliding carrier 46, so that fore and aft movement of the carrier 46 in the track 48 affects sliding movement of the inner catheter body 24 (as FIGS. 4A and 5 show). In response to forward movement of the carrier 46 (as FIG. 4A shows), the inner catheter body 24 slides in a distal direction within the outer catheter body 26. In response to aft movement of the carrier 46 (as FIG. 5 shows), the inner catheter body 24 slides in a proximal direction within the outer catheter body 26.

A spring biased latch mechanism 50 is desirably coupled to the carrier 46. The latch mechanism 50 snap-fits into detents 52 (shown in FIG. 2) at the proximal and distal ends of the track 48, to releasably lock the carrier 46 against movement. Finger pressure releases the spring biased latch mechanism 50 from the detents 52, to release the carrier 46 for movement between the proximal and distal detents 52.

Figure 6:
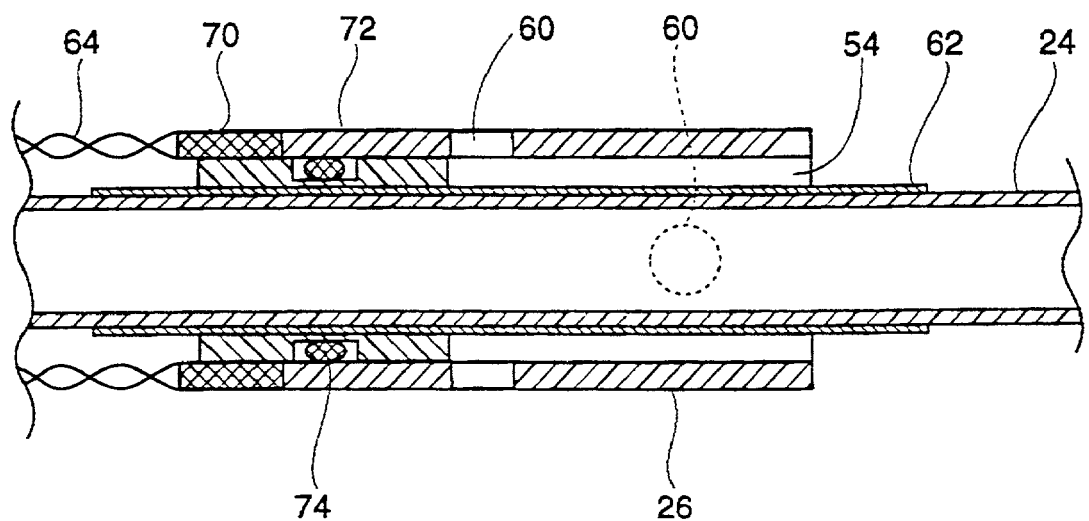
FIG. 6 is an enlarged side section view of the junction between the expandable structure and the outer catheter body of the catheter assembly shown in FIGS. 4A and 5.

The interior diameter of the outer catheter body 26 (see FIGS. 3 to 5) is larger than the exterior diameter of the inner catheter body 24. In interior passage 54 is thereby defined between them (see FIG. 3). A port 56 on the handle 38 communicates with the passage 54 (see FIG. 2). The port 56 terminates with the component introducer/mixer assembly 22 through intermediate tubing 58. Liquid components introduced through the assembly 22 exit the passage 54 through one or more nozzles 60 formed near the distal end of the outer catheter body 26 (see FIG. 6). As FIGS. 3 and 6 show, a thin wall tube 62 (extruded, e.g., from a polyimide material) desirably covers the inner catheter body 24, to prevent liquid components within the passage 54 from adhesively bonding the inner catheter body 24 to the outer catheter body 26. Free sliding motion of the inner catheter body 24 within the tube 62 is thereby preserved.

Figure 7B:
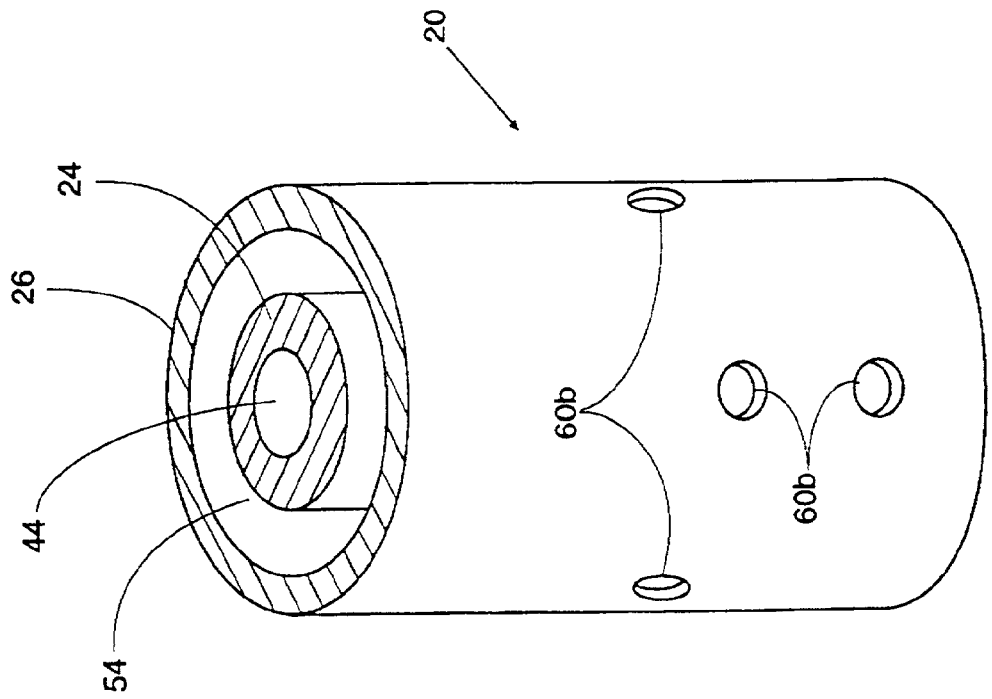
FIGS. 7A and 7B are perspective views of alternative arrays of composition delivery nozzles located on the catheter assembly that forms a part of the vascular puncture site access assembly shown in FIG. 1.
Figure 7A:
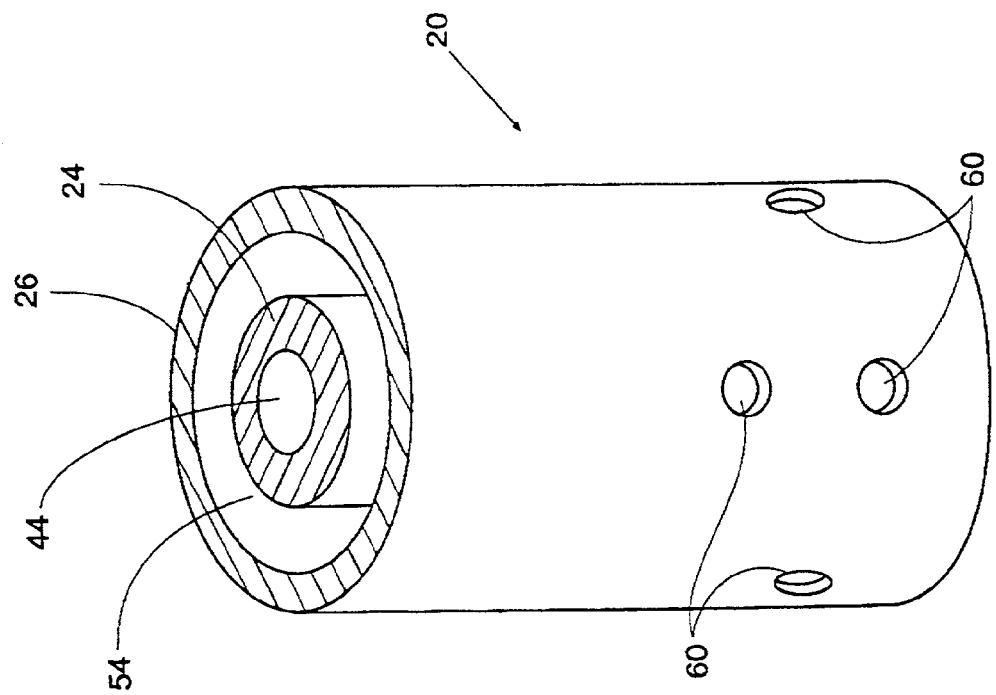

The nozzles 60 can be arranged in different delivery patterns. In one embodiment (as FIG. 7A shows), an array of nozzles 60, circumferentially spaced apart, is provided. In another embodiment (as FIG. 7B shows), the nozzles 60A and 60B are spaced apart along the axis of the outer catheter body 26, as well as being staggered to face different directions about the axis.

The diameter of the nozzles 60 can also vary (e.g., from 0.02" to 0.0351"). The nozzles 60 can all share the same diameter. Alternatively, the nozzles 60 can have different diameters, to create preferential flow patterns (the liquid composition following the path of less flow resistance in preference to a path of greater flow resistance).

It is desired that the nozzles 60 reside outside the blood vessel when the material composition is introduced. To help locate the nozzles 60 outside the blood vessel, the catheter assembly 20 includes an expandable structure 64 located near to and distally of the nozzles 60 (see FIGS. 4A and 5).

The wall 66 of the structure 64 desirably comprises an open or woven or braided structure comprising interlaced or intersecting strands or threads 68 (see FIG. 4B), e.g., made from an inert biocompatable polymeric material, such as nylon. Alternatively, the outer catheter body 26 can itself be slotted at circumferentially spaced locations to form the structure 64. The proximal end of the structure 64 is secured (see FIG. 6), e.g., by a fuse joint 70, about a gland member 72 that encircles the thin wall tube 62. As FIG. 6 also shows, the distal end of the outer catheter body 26 is also secured, e.g., by adhesive, to the gland member 72. An o-ring 74 is also desired placed within the gland member 72 to prevent leakage of liquid components from the passage 54 into the interior of the structure 64.

The distal end of the structure 64 is secured, e.g., by adhesive or a shrink-fit sleeve, to a region of the inner catheter body 24 that extends beyond the outer catheter body 26. The inner catheter body 24 also extends a distance distally beyond the structure 64, forming a leader 76 (see FIGS. 4A and 5). In use, the leader 76 is located inside the blood vessel immediately interior to the puncture site 36 (like the leader 76 in FIGS. 19 and 20). In use, the array of nozzles 60 is located outside the blood vessel exterior to the puncture site 36 (like the nozzles 60 in FIG. 20). Sliding movement of the inner catheter body 24 relative to the outer catheter body 26 serves to mechanically expand (see FIG. 5) and collapse (see FIG. 4A) the structure 64, so that this desired positioning of the nozzles 60 and leader 76 can be achieved.

Since, in the illustrated embodiment, the structure 64 possesses a wall that is open or woven, the structure 64 permits blood flow through it, thereby presenting a minimal disruption of blood flow in the vessel during use. Due to the open or woven configuration of the structure 64, the positioner can be deployed in an expanded state within the artery prior to being seated against the interior of the vessel wall, with minimal disruption of blood flow. This allows the physician to proceed with the deployment and positioning of the structure 64 within the vessel in a deliberate fashion, without being rushed due to ancillary considerations of attendant blood flow disruption. The open structure 64 can be deployed while a patient is in an operating room, and left deployed while the patient is wheeled from the operating room to another suite, where the vessel closure procedure is completed. In this way, the operating room, its staff, and its equipment are made available for another procedure while the vessel closure procedure is completed in another setting by a medically trained person, who need not be a medical doctor.

Desirably, radiopaque marker bands 78 are secured to the proximal and distal ends of the structure 64, as well as to the distal-most end of the leader 76. Preferably, the three markers 78 appear at equidistant intervals when the structure 64 is in its collapsed or stowed condition. Thus, when the structure 64 is in its expanded condition, the markers 78 no longer appear equidistant. In this way, the physician can readily gauge by fluoroscopy the location of the distal-most end of the inner catheter body 24, as well as the distance between the ends of the structure 64 and, thereby, assess the position and configuration of the inner catheter body 24 and the structure 64 near the puncture site 36.

The Component Introducer/Mixer Assembly

Before mixing, the components for the material composition are housed in the formative component assembly 18 contained in the kit 14 (see FIG. 1), which will be described in greater detail later.

Figure 10:
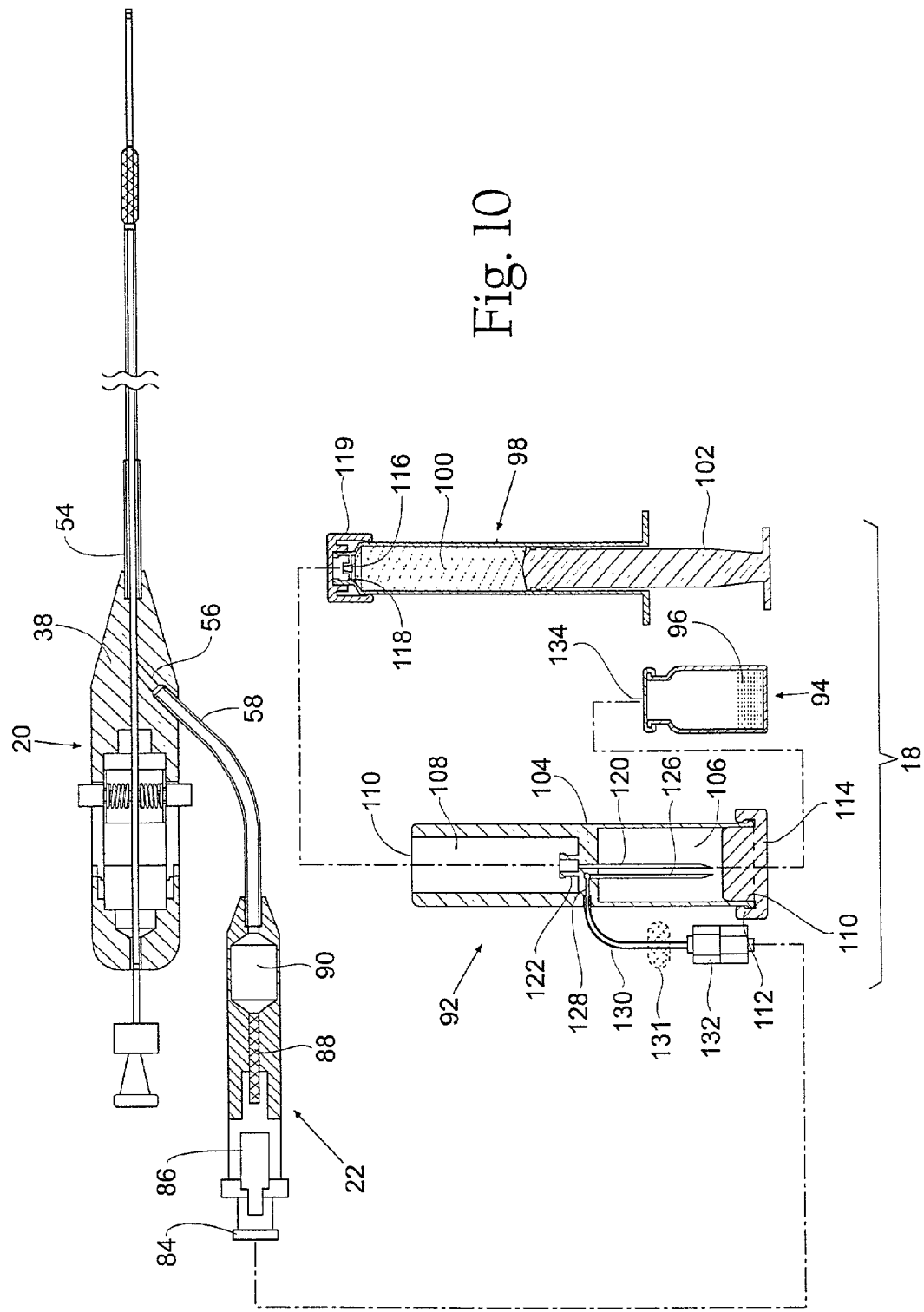
FIG. 10 is a perspective view of the individual components of the formative component assembly shown in FIG. 1 and further illustrating the catheter assembly shown in FIG. 2 and the introducer/mixer assembly shown in FIG. 1 coupled together.

As FIG. 10 shows, the proximal end of the introducer/mixer assembly 22 includes a length of flexible intermediate tubing 58 that couples to the port 56 of the y-adapter/handle 38. The distal end of the assembly 22 includes a luer fitting 84 that couples to the formative component assembly 18 (see also FIG. 13).

Communicating with the tubing 58 in the direction of flow into the passage 54, are an in-line syringe activated check valve-86, an in-line mixer 88, and an in-line air accumulator 90.

The in-line syringe activated check valve 86 can take various forms. In the illustrated embodiment, the valve 84 takes the form of a conventional, needleless slip luer lock valve made by Qosina (Edgewood, N.Y.), Product Number 80360. The valve 84 is normally closed to prevent back flow of blood or other liquid material through the tubing 58. Back flow of blood, in particular, from the passage is undesirable, as it creates the potential for blood contact and deposits material in the introducer/mixer assembly 22 that can interfere or compete with the desired reaction between the liquid components that form the material composition. Connection of a conventional luer fitting carried by the formative component assembly 18 (for example, fitting 132 shown in FIGS. 10 and 13) opens the valve 86 to allow the introduction of the liquid components that form the material composition.

The components of the material composition come into contact in the liquid state in the in-line mixer 88. In this way, effective mixing can be achieved outside the catheter assembly 20 that is not dependent solely upon the dimensions or lengths of the flow paths within the catheter assembly 20. The mixer 88 comprises a mixing structure, which can vary. For example, the mixer 88 can comprise a spiral mixer manufactured by TAH Industries, Inc. (Robbinsville, N.J.), Part Number 121-090-08.

The in-line air accumulator 90 comprises a chamber that has an interior volume sized to trap air that can reside in the material composition applicator at time of use.

The Formative Component Assembly

The components forming the material composition can vary. Generally speaking, however, the components will include a solid component and a liquid component, which serves as a diluent for the solid component. Mixing of these two components initiates a chemical reaction, by which the liquid mixture transforms into a solid composition. It is the purpose of the formative component assembly 18 to facilitate the mixing of these two components and introduction of the mixture into the introducer/mixer assembly 22 and delivery to the catheter assembly 20.

The formative component assembly 18 can comprise individual syringes in which the components are separately contained. Further details of this arrangement are disclosed in copending U.S. patent application Ser. No. 09/187,384, filed Nov. 6, 1998 and entitled "Systems and Methods for Applying Cross-Linked Mechanical Barriers," which is incorporated herein by reference.

Figure 8:
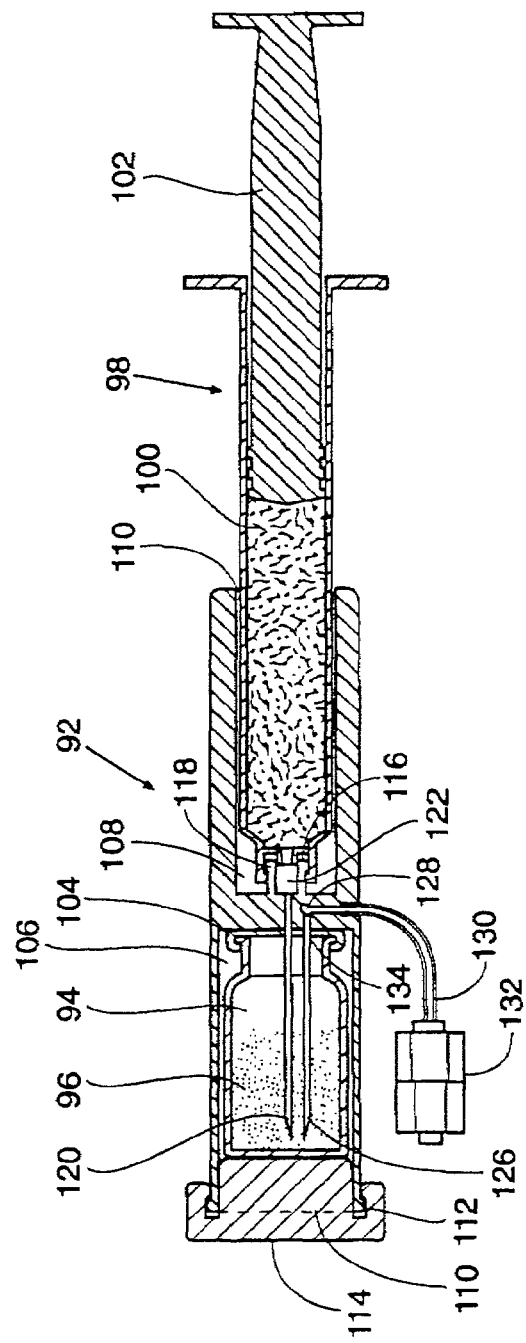
FIG. 8 is an assembled section view of the components of formative component assembly shown in FIG. 1.

With reference to FIG. 8, an alternative arrangement provides a unitary applicator 92 in which a vial 94 holding a solid component 96 and a syringe 98 holding a liquid component 100 can be placed and kept separate in interior compartments.

Axial advancement of the syringe plunger 102 propels the liquid 100 into the vial 94 and brings the two components 96 and 100 together within the vial 94 by placing the solid component 96 into suspension within the liquid component 100. The force created by this process also urges the liquid suspension into the introducer/mixer assembly 22 for further mixing and delivery to the catheter assembly 20.

The applicator 92 includes a partition 104 that divides the applicator 92 into a first compartment 106 and a second compartment 108, each having an open end 110. The first compartment 106 is sized and configured to receive and hold the vial 94. The first compartment 106 includes a flanged end region 112 that serves to support the applicator 92 in an upright position (e.g., standing on a table). The flanged region 112 further serves to receive a cap 114, as will be described in greater detail later. The second compartment 108 is sized and configured to receive and hold the syringe 98. While the illustrated embodiment shows the applicator 92 and compartments 106 and 108 having a generally cylindrical shape, the invention contemplates other configurations not necessarily accommodating a vial 94 and/or syringe 98.

The applicator 92 can be made of any suitable inert, rigid plastic or metal material. In a representative embodiment, the first compartment 106 is 2½ inches long, the second compartment 108 is 2 inches long, and the applicator 92 is 1 inch high. This arrangement readily accommodates a conventional vial 94 and a conventional syringe 98.

The syringe 98 can be a conventional syringe 98 having a plunger 102. The dispensing end 116 includes a luer fitting 118. The syringe 98 is aseptically pre-filled with the liquid component 100 and a cap 119 is placed over the dispensing end 116 to prevent leakage and evaporation of the contents.

Figure 9:
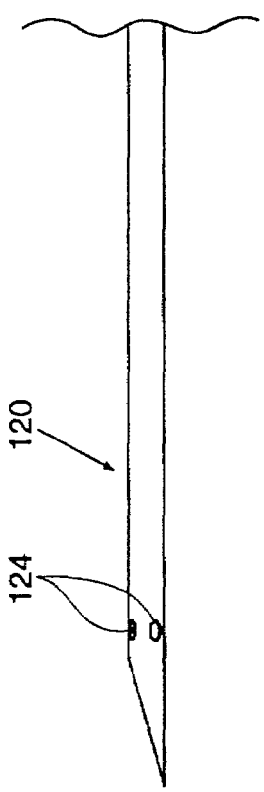
FIG. 9 is an enlarged view illustrating the arrangement of side holes in the first needle of the formative component assembly shown in FIG. 1.

A first needle 120 extends along the central line axis of the applicator 92 and couples the syringe 98 to the vial 94 via a luer fitting 122 that mates with the luer fitting 118 on the syringe 98. The needle 120 thereby provides communication between the first and second compartments 106 and 108. Desirably, the needle 120 includes a plurality of side holes 124 that serve to uniformly introduce the contents of the syringe 98 into the vial 94 (see FIG. 9).

A second needle 126 is offset from the central line axis of the applicator 92 and serves to couple the vial 94 to a molded passage 128 that traverses the wall of the second compartment 108. The molded passage 128 is coupled to the proximal end of a length of flexible tubing 130. The distal end of the tubing 130 includes a luer fitting 132 adapted to couple to the leur fitting 84 on the introducer/mixer assembly 22. This arrangement provides fluid communication between the vial 94 and the introducer/mixer assembly 22. Optionally, an in-line air vent 131 (shown in phantom lines in FIG. 10), made, e.g., from a sintered plastic material, can be located in the tubing 130, or otherwise placed in communication with the tubing 130, to allow residual air to vent from fluid prior to entering the introducer/mixer assembly 22.

The vial 94 is a conventional pharmaceutical vial 94 sized to hold the solid component 96 and a pre-defined volume of the liquid component 100, i.e., the volume of liquid component 100 pre-filled in the syringe 98. The vial 94 includes a septum 134 configured to be pierced and penetrated by the needles 120 and 126 when the vial 94 is properly positioned within the first compartment 106.

To aid in positioning and securing of the vial 94 within the compartment 106, the applicator 92 includes a selectively removable cap 114, as previously noted. The cap 114 mates with the applicator 92, e.g., by snap-fit engagement with the flanged region 112 on the applicator 92. Desirably, the cap 114 extends into the first compartment 106 to position and hold the vial 94 in a desired position after the septum 134 has been pierced by the needles 120 and 126.

Figure 11A:
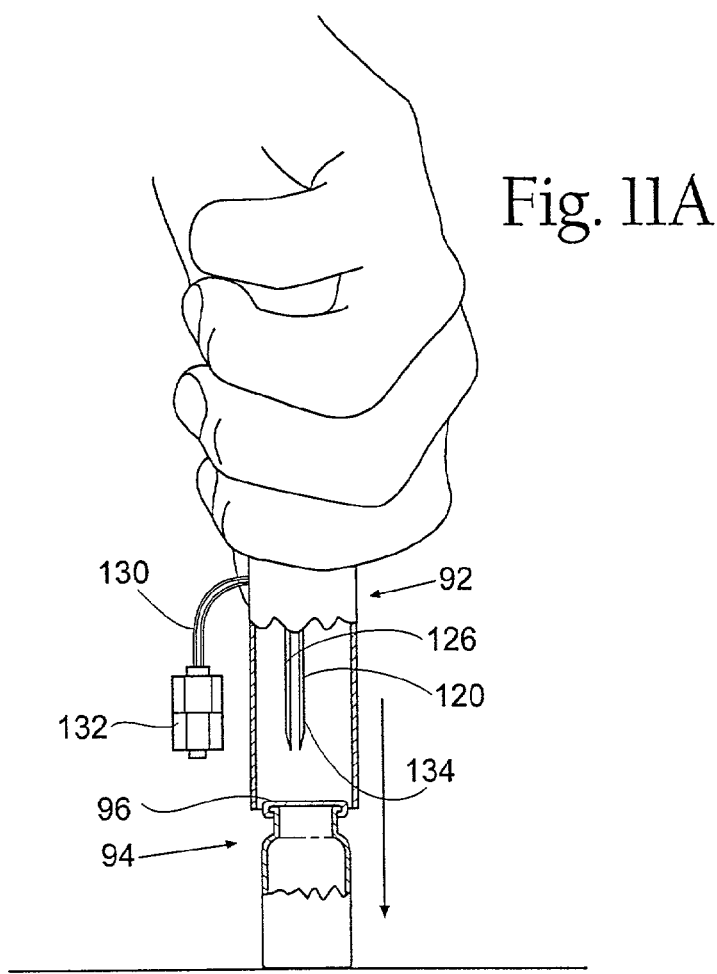
FIGS. 11A and 11B are perspective views illustrating the insertion of the vial component of the formative component assembly shown in FIG. 1 into to the applicator component.
Figure 11B:
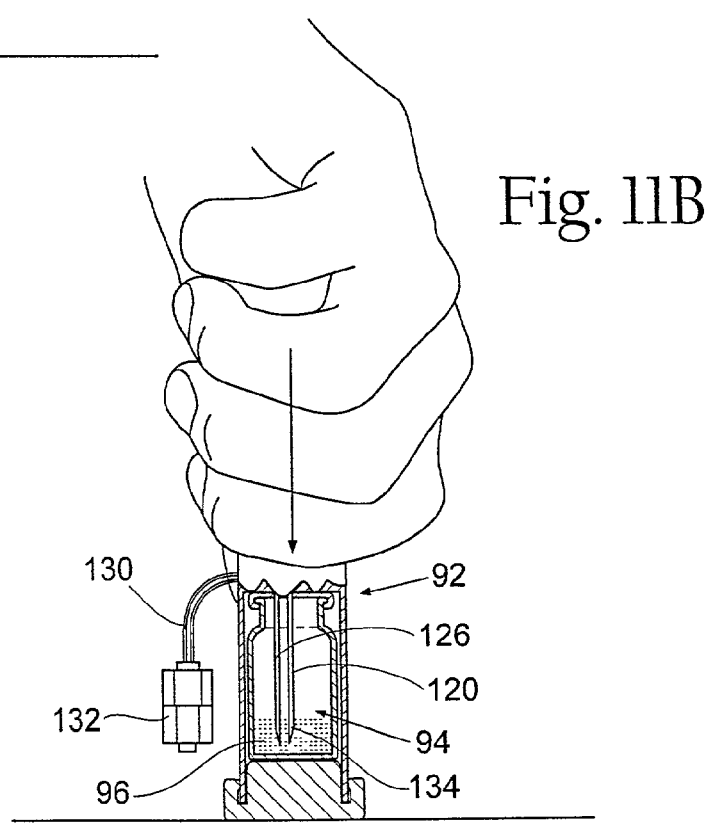

FIG. 10 shows the individual components of the formative component assembly 18. In use, the physician (or assistant) removes the cap 114 from the applicator 92. As seen in FIG. 11A, with the cap 114 removed, the physician slides the first compartment 106 over the vial 94. During this step, the vial 94 can be placed on a counter, table, or other flat support surface. As seen in FIG. 11B, the cap 114 is then placed beneath the vial 94 (e.g., on the counter or table), and the physician continues to slide the first compartment 106 over the vial 94, to finish piercing the vial septum 134 with the needles 120 and 126 and locating the vial 94 fully into the first compartment 106. The cap 114 thereafter holds the vial 94 in this position.

The cap 119 is then removed from the syringe 98 and residual air is expressed from the syringe 98, e.g., by holding the syringe 98 with the dispensing end 116 upright and gently tapping the syringe 98 until essentially all of the residual air rises to the dispensing end 116 and then advancing the plunger 102 until the air is expelled (not shown).

Figure 12:
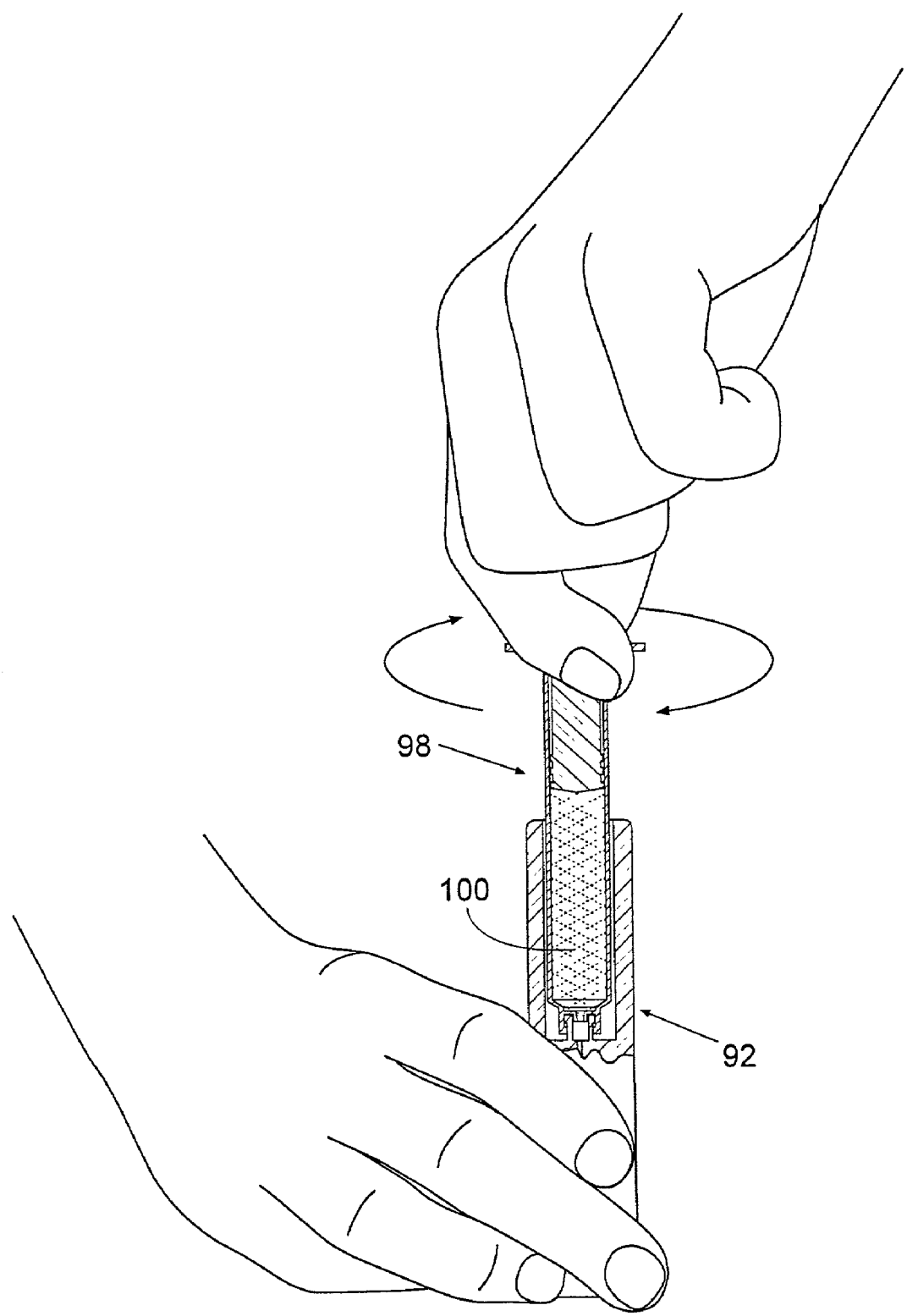
Figure 13:
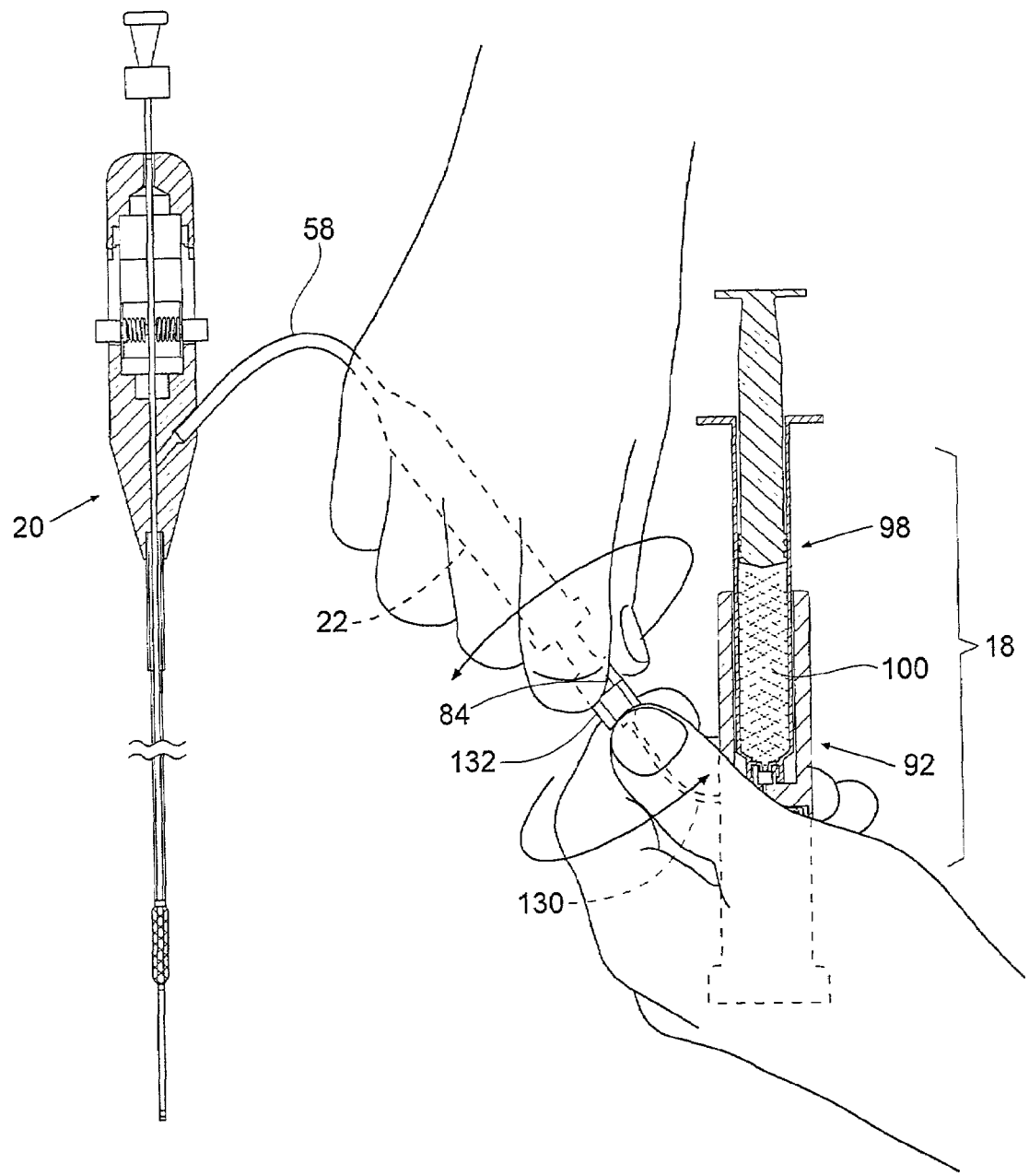

As FIG. 12 shows, the syringe 98 is then placed within the second compartment 108 and rotated (represented by arrow) to couple the syringe 98 to the first needle 120 through leur fittings 118 and 122. With the syringe 98 and vial 94 in place within the applicator 92 and the formative assembly 18 ready for use, as seen in FIG. 13, the assembly 18 can then be coupled to the introducer/mixer assembly 22 (shown in phantom lines) by coupling (represented by arrows) leur fittings 84 and 132.

As will be apparent, alternatively, the syringe 98 can be coupled to the first needle 120 prior to the vial 94 being placed in the first compartment 106.

Figure 14:
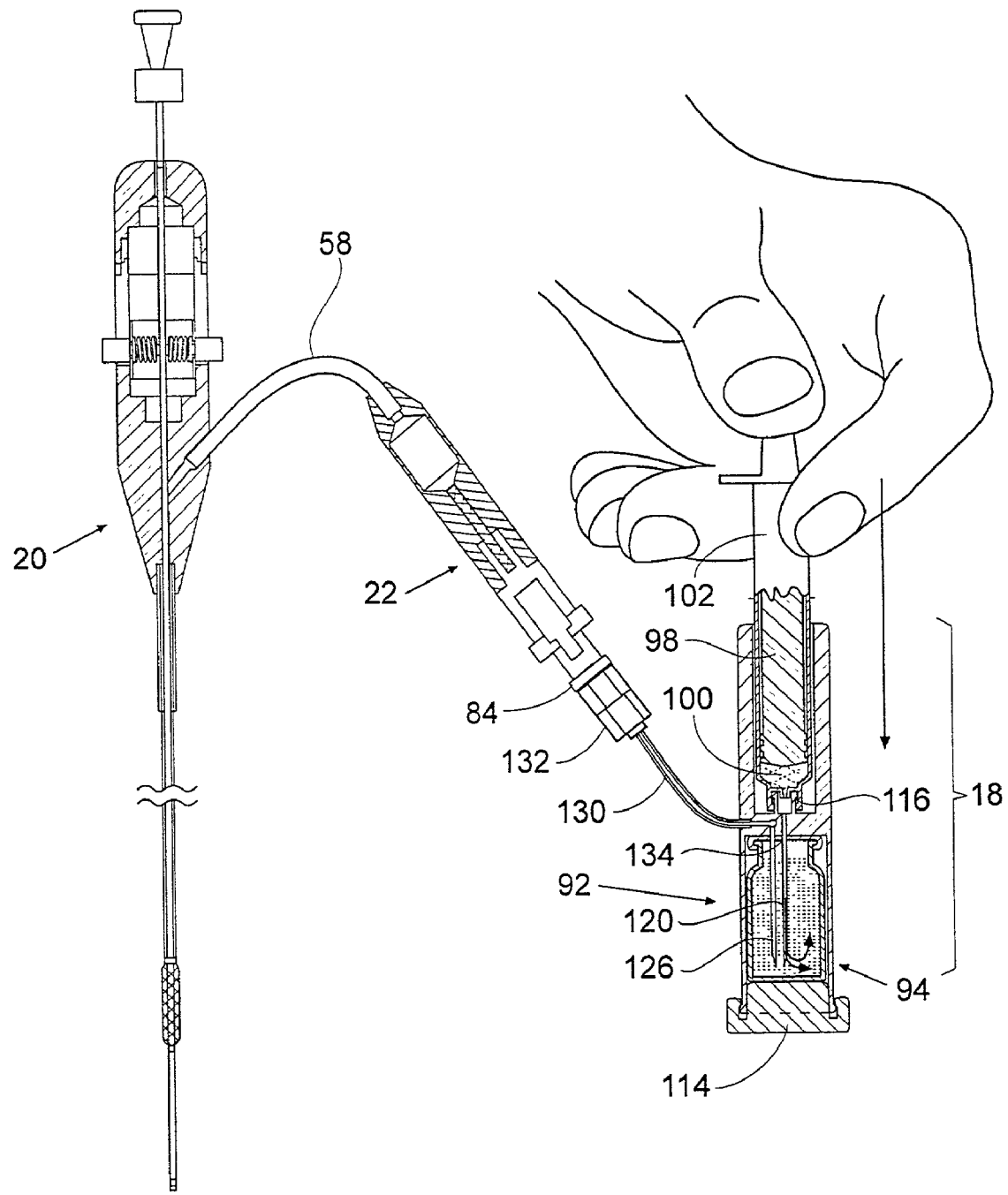

With reference now to FIG. 14, the formative component assembly 18 is then placed in an upright position (i.e., vial septum 134 pointing upward and dispensing end 116 of the syringe 98 pointing downward). The plunger 102 is then advanced (represented by arrow) to transfer the contents of the syringe 98 through the first needle 120 into the vial 94. If desired, the assembly 18 can be stood on a counter, table, or other flat surface as the plunger 102 is advanced. Alternatively, the plunger 102 can be advanced in conventional fashion by the thumb of the physician while the syringe 98, with attached applicator 92, are held between the forefinger and middle finger, as FIG. 14 shows.

The propulsion of the liquid component 100 into the vial 94 reconstitutes the solid component 96, mixes the components 96 and 100 (represented by arrows in FIG. 14), and begins the reaction process. As previously noted, side holes 124 in the first needle 120 assure components 96 and 100 mix quickly and uniformly (see FIG. 9).

Figure 15:
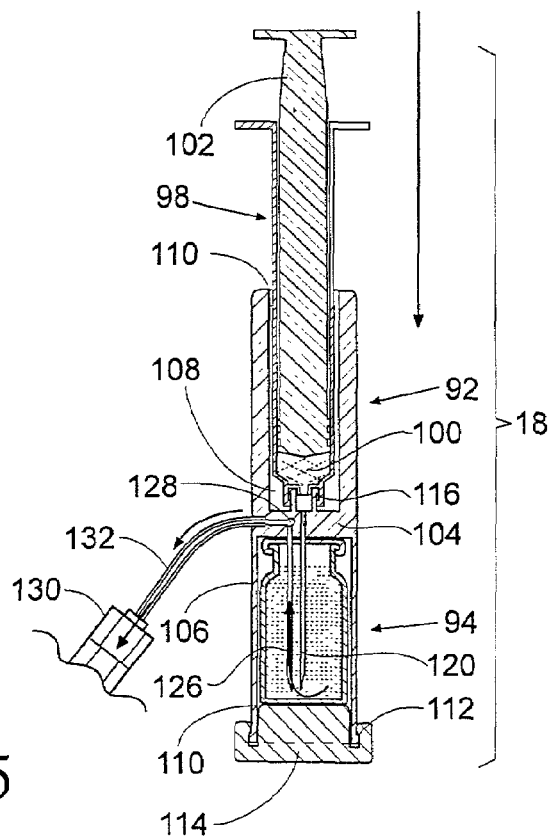

Fluid pressure created by operation of the syringe 98 urges the mixture into and through the second needle 126, into the introducer/mixer assembly 22, as indicated by arrows in FIG. 15. The introducer/mixer assembly 22 further mixes the mixture and rids the fluid path of residual air, as previously described. The mixture flows through the introducer/mixer assembly 22 and through the catheter assembly 20 and exits the assembly 22 through the nozzles 60, as also previously described.

Figure 16:
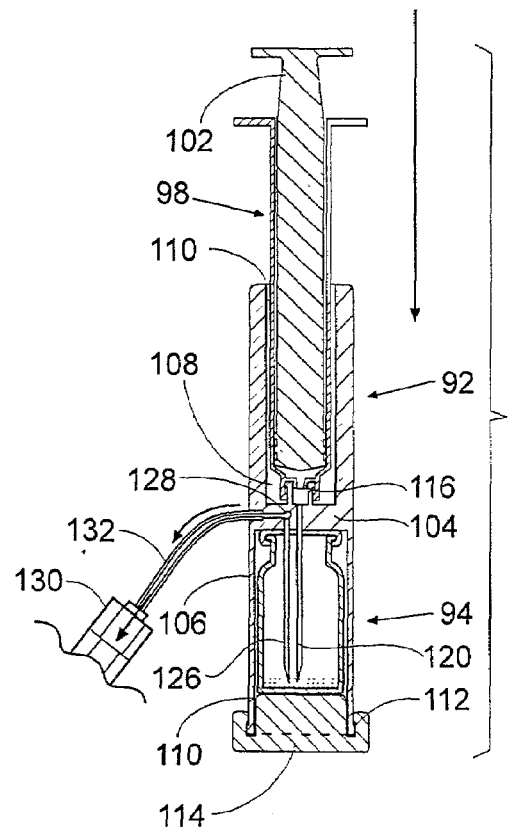

With reference now to FIG. 16, the plunger 102 is advanced until essentially all of the liquid component 100 is transferred from the syringe 98 to the vial 94. Generally concurrently, the mixture is transferred from the vial 94 into the introducer/mixer 22, with only minimal residual mixture remaining in the vial 94. As will apparent to one skilled in the art, the volume of components 96 and 100 are calculated to account for this residual volume.

It should be appreciated that the applicator 92 can be coupled to diverse forms of fluid delivery systems. It can, as shown, be coupled to a catheter-based system. It can alternatively, depending upon the indicated use, be coupled to a spray applicator or to a cannula.

The Material Composition

The components 96 and 100 of the material composition can vary. In a preferred embodiment, the solid component 96 comprises an electrophilic (electrode withdrawing) material having a functionality of at least three. The liquid component 100 comprises a solution containing a nucleophilic (electron donator) material and a buffer. When mixed under proper reaction conditions, the electrophilic material and buffered nucleophilic material react, by cross-linking with each other. The cross-linking of the components form the composition. The composition physically forms a mechanical barrier 136 (see FIG. 22), which can also be characterized as a hydrogel.

The type and concentration of the buffer material controls the pH of the liquid and solid components 100 and 96, when brought into contact for mixing. The buffer material desirably establishes an initial pH in numeric terms, as well regulates change of the pH over time (a characteristic that will be called the "buffering capacity").

The barrier composition 136 exhibits desired mechanical properties. These properties include adhesive strength (adhering it to adjacent tissue), cohesive strength (forming a mechanical barrier that is resistant to blood pressure and blood seepage), and elasticity (accommodating the normal stresses and strains of everyday activity). These properties, as well as the relative rapid rate of gelation that can be achieved, serve to provide a fast and effective closure to the vascular puncture site.

The barrier composition 136 is also capable of transforming over time by physiological mechanisms from the solid state to a biocompatible liquid state, which can be cleared by the body, in a process called "degradation."

The time period that begins when the electrophilic, nucleophilic, and buffer components have been mixed and ends when the composition has reached the semi-solid (gel) state will be called the "gelation time." When in this state, the barrier composition 136 possesses sufficient cohesive and adhesive strength to impede blood flow, but still retains a self-sealing property, possessing the capacity to close in upon and seal the tract left by the catheter in the composition when the physician removes the catheter. For sealing a vascular puncture site, the barrier composition 136 preferably possesses a gelation time that is in the range of fifteen to sixty seconds. A gelation time in the range of fifteen to thirty seconds is most preferred. This period allows the components forming the barrier composition 136 to flow first in a liquid state, and then in the semi-solid (gel) state, outward along the axis of the blood vessel. The flow of components during gelation fills surface irregularities in the tissue region of the vascular puncture site, before solidification occurs. A gelation time period of between 10 and 40 seconds also falls well within the time period a physician typically needs to manipulate and remove the catheter assembly 20 after delivery of the components to the puncture site 36. With an experienced physician, the catheter manipulation and removal time period can be as quick as 10 to 40 seconds, but it can extend, due to circumstances, upwards to 2 minutes. With a gelation time falling within the preferred range, the formation of the barrier composition does not require a physician to "watch the clock," but rather attend only to the normal tasks of injecting the material and then manipulating and removing the catheter assembly. With a gelation time falling within the preferred range, it has been discovered that, if the catheter assembly 20 is removed in 15 seconds to 2 minutes following initial mixing, the barrier composition 136 has reached a physical state capable of performing its intended function, while still accommodating a sealed withdrawal of the catheter assembly 20. Desirably, after removal of the catheter assembly 20, the physician applies localized and temporary finger pressure to the skin surface above the barrier composition 136 for a period of about 5 minutes, to aid in the closure of the catheter tract in the composition, as the composition 136 reaches its solid state.

The barrier composition 136 preferably possesses sufficient adhesive strength to prevent dislodging from the arteriotomy, once formed. The composition 136 also has sufficient cohesive strength to prevent rupture under arterial pressure, i.e., up to about 200 mm Hg. The barrier composition 136 seals the arteriotomy for up to 15 days post-application before loss of mechanical properties through degradation, and degrades by 30 to 90 days post-application.

The gelation time (which indicates the rate at which the cross-linking reaction occurs) is controlled, inter alia, by the reaction pH, which the buffer component establishes. The reaction pH controls the reactivity of nucleophilic groups in the second component 100, which react with the electrophilic groups in the first component 96. Generally speaking, the higher the reaction pH is, the larger is the fraction of nucleophilic groups available for reaction with the electrophilic groups, and vice versa.

To achieve a relatively rapid gelation time, a relatively high initial reaction pH (which, for the illustrated components, is above 8) is desirable at the time initial mixing of the components occurs. On the other hand, by the time the mixture is brought into contact with body tissue at the vascular puncture site, it is desirable that the mixture possess a more physiologically tolerated pH level (approximately 7.4).

However, it has been discovered that, if the initial reaction pH is too high (which, for the illustrated components, is believed to be a pH approaching about 9), the gelation time may be too rapid to consistently accommodate the time period a physician typically requires to remove the catheter, particularly if the time period approaches the two minute mark. In this instance, by the two minute mark, substantial solidification of the composition 136 can occur, and the composition 136 can lack the cross-linking capacity to close in about the catheter tract left in the composition upon removal of the catheter. Under these circumstances, blood leakage and hematoma formation can result after removal of the catheter assembly 20.

Achieving and sustaining a reaction pH to meet a targeted gelation time is therefore a critical criteria. It has been discovered that, by purposeful selection of the electrophilic, nucleophilic, and buffer components, (i) an initially high reaction pH can be established that is conducive to rapid gelation, before contact with body tissue occurs, and (ii) the reaction pH can be lowered as gelation progresses, as the mixture is delivered through the catheter into contact with body tissue at the vascular puncture site 36. At the same time, by purposeful selection of the components, the rate at which the pH is lowered during delivery can be mediated, so that gelation is sustained at a rate that meets the gelation time requirements to achieve the desired in situ formation of the composition 136, one that also possesses sufficent cross-linking capacity to close about the catheter tract following removal of the catheter assembly 20 after a time period a physician typically needs to perform this task.

The Electrophilic Component

In its most preferred form, the electrophilic (electrode withdrawing) material 96 comprises a hydrophilic, biocompatible polymer that is electrophilically derivatized with a functionality of at least three. Examples include poly(ethylene glycol), poly(ethylene oxide), poly(vinyl alcohol), poly(vinylpyrrolidinone), poly(ethyloxazoline), and poly(ethylene glycol)-co-poly(propylene glycol) block copolymers.

As used herein, a polymer meeting the above criteria is one that begins with a multiple arm core (e.g., pentaerythritol) and not a bifunctional starting material, and which is synthesized to a desired molecular weight (by derivatizing the end groups), such that polymers with functional groups greater than or equal to three constitute (according to gel permeation chromatography—GPC) at least 50% or more of the polymer blend.

The material 96 is not restricted to synthetic polymers, as polysaccharides, carbohydrates, and proteins could be electrophilically derivatized with a functionality of at least three. In addition, hybrid proteins with one or more substitutions, deletions, or additions in the primary structure may be used as the material 96. In this arrangement, the protein's primary structure is not restricted to those found in nature, as an amino acid sequence can be synthetically designed to achieve a particular structure and/or function and then incorporated into the material. The protein of the polymer material 96 can be recombinantly produced or collected from naturally occurring sources.

Preferably, the polymer material 96 is comprised of poly(ethylene glycol) (PEG) with a molecular weight preferably between 9,000 and 12,000, and most preferably 10,500±1500. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of solutions, but sterile water is preferred.

The most preferred polymer material 96 can be generally expressed as compounds of the formula:

Where:
DCR is a degradation control region.
CG is a cross-linking group.
$n \geq 3$ The electrophilic CG is responsible for the cross-linking of the preferred nucleophilic material 96, as well as binding the composition 136 to the like material in the surrounding tissue, as will be described later. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate. The preferred CG's are active esters, more preferred, an ester of N-hydroxysuccinimide. The active esters are preferred since they react rapidly with nucleophilic groups and have a non-toxic leaving group, e.g., hydroxysuccinimide.

The concentration of the CG in the polymer material 96 can be used to control the rate of gelation. However, changes in this concentration typically also result in changes in the desired mechanical properties of the hydrogel.

The rate of degradation is controlled by the degradation control region (DCR), the concentration of the CG's in the polymer solution, and the concentration of the nucleophilic groups in the protein solution. Changes in these concentrations also typically result in changes in the mechanical properties of the hydrogel, as well as the rate of degradation.

The rate of degradation (which desirably occurs in about 30 days) is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly(glycolic acid), poly(DL-lactic acid), poly(L-lactic acid), poly(ξ-caprolactone), poly(δ-valerolactone), poly(γ-butyrolactone), poly(amino acids), poly(anhydrides), poly(orthoesters), poly(orthocarbonates), and poly(phosphoesters), and derivatives thereof. A preferred hydrolytically degradable DCR is gluturate. Examples of enzymatically degradable DCR's include Leu-Gly-Pro-Ala (collagenase sensitive linkage) and Gly-Pro-Lys (plasmin sensitive linkage). It should also be appreciated that the DCR could contain combinations of degradable groups, e.g. poly(glycolic acid) and di-acid.

While the preferred polymer is a multi-armed structure, a linear polymer with a functionality, or reactive groups per molecule, of at least three can also be used. The utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

A preferred polymer may be purchased from SunBio Company ((PEG-SG)4, having a molecular weight of 10,500±1500) (which will sometimes be called the "SunBio PEG").

The Nucleophilic Component

In a most preferred embodiment, the nucleophilic material 100 includes non-immunogenic, hydrophilic proteins. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the nucleophilic material 100. The protein can be recombinantly produced or collected from naturally occurring sources.

The preferred protein solution is 25% human serum albumin, USP. Human serum albumin is preferred due to its biocompatibility and its ready availability.

The uses of PEG polymers with functionality of greater than three provides a surprising advantage when albumin is used as the nucleophilic material 100. When cross-linked with higher functionality PEG polymers, the concentration of albumin can be reduced to 25% and below. Past uses of difunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

To minimize the liberation of heat during the cross-linking reaction, the concentration of the cross-linking groups of the fundamental polymer component is preferably kept less than 5% of the total mass of the reactive solution, and more preferably about 1% or less. The low concentration of the cross-linking group is also beneficial so that the amount of the leaving group is also minimized. In a typical clinical application, about 50 mg of a non-toxic leaving group is produced during the cross-linking reaction, a further desired result. In a preferred embodiment, the CG comprising an N-hydroxysuccinimide ester has demonstrated ability to participate in the cross-linking reaction with albumin without eliciting adverse immune responses in humans.

The Buffer Component

In the most preferred embodiment, a PEG reactive ester reacts with the amino groups of the albumin and other tissue proteins, with the release of N-hydroxysuccinimide and the formation of a link between the PEG and the protein. When there are multiple reactive ester groups per PEG molecule, and each protein has many reactive groups, a network of links form, binding all the albumin molecules to each other and to adjacent tissue proteins.

This reaction with protein amino groups is not the only reaction that the PEG reactive ester can undergo. It can also react with water (i.e., hydrolyze), thereby losing its ability to react with protein. For this reason, the PEG reactive ester must be stored dry before use and dissolved under conditions where it does not hydrolyze rapidly. The storage container for the PEG material desirably is evacuated by use of a vacuum, and the PEG material is stored therein under an inert gas, such as Argon or Nitrogen. Another method of packaging the PEG material is to lyophilize the PEG material and store it under vacuum, or under an inert gas, such as Argon or Nitrogen, as will be described in greater detail later. Lyophilization provides the benefits of long term storage and product stability, as well as allows rapid dissolution of the PEG material in water.

The conditions that speed up hydrolysis tend to parallel those that speed up the reaction with protein; namely, increased temperature; increased concentration; and increased pH (i.e., increased alkali). In the illustrated embodiment, temperature cannot be easily varied, so varying the concentrations and the pH are the primary methods of control.

It is the purpose of the buffer material (which is added to the nucleophilic albumin material 100 prior to mixing with the electrophilic PEG material 96) to establish an initial pH to achieve a desired gelation time, and to sustain the pH as added acid is produced by the release of N-hydroxysuccinimide during cross linking and hydrolysis.

pH is the special scale of measurement established to define the concentration in water of acid (H+) or alkali (OH−) (which, strictly speaking, indicates hydrogen ion activity). In the pH scale, solutions of acid (H+) in water have a low pH, neutrality is around pH 7, and solutions of base (OH−) in water have a high pH. The pH scale is logarithmic. A change of one pH unit (e.g., from pH 9 to pH 10) corresponds to a ten-fold change in concentration (i.e., hydrogen ion activity). Thus, reactions which are increased by alkali, such as hydrolysis of PEG reactive ester, are expected to increase in rate by a factor of ten for each unit increase in pH.

The buffer material is a mixture of molecules, added to the albumin, that can moderate pH changes by reacting reversibly with added acid (H+) or base (OH−). The pH moderating effect can be measured by titration, i.e., by adding increasing amounts of H+ or OH− to the buffer material, measuring the pH at each step, and comparing the pH changes to that of a similar solution without the buffer.

Different buffers exert a maximum pH moderating effect (i.e., the least change in pH with added H+ or OH−) at different pH's. The pH at which a given buffer exerts its maximum pH moderating effect is called its pK.

Even when the pH matches the pK for a given buffer, added acid or base will produce some change in pH. As the pH changes from the pK value, the moderating effect of the buffer decreases progressively (e.g., 67% less at +/−1 pH unit from pK, and 90% less at +/−1.6 pH unit from pK). The moderating effect is also proportional to the buffer concentration. Thus, increasing the buffer concentration increases the ability to moderate pH changes.

The overall buffering effect at any pH is the sum of all buffering species present, and has also been earlier called the buffering capacity. The higher the buffering capacity, the more acid or base must be added to produce a given pH change. Stated differently, the higher the buffering capacity, the longer a given buffer is able to sustain a targeted pH range as acid or base is being added to change the pH.

Albumin itself contains amino, carboxyl, and other groups, which can reversible react with acid and base. That is, albumin itself is a buffer. Also, due to the many different buffering groups that albumin possesses, albumin (e.g., Plasbumin) can buffer over a relatively broad pH range, from below pH 6 to over pH 10. However, it has been discovered that albumin lacks the buffering capacity to, by itself, counterbalance the additional acid (H+) that is produced as a result of hydrolysis and the PEG-albumin cross-linking, given the PEG concentrations required to meet the therapeutic objectives for the composition. Thus, in the preferred embodiment, a buffer material must be added to the albumin to provide the required buffering capacity.

The buffer material must meet several criteria. The buffer material must be (1) non-toxic, (2) biocompatible, (3) possess a pK capable of buffering in the pH range where the desirable gelation time exists, and (4) must not interfere with the reaction of protein with the selected PEG reactive ester. Amine-containing buffers do not meet criteria (4).

To meet criteria (3), the buffer material should have a buffering capacity at the desired cross-linking pH (i.e., according todicated by its pK) that is high enough to counterbalance the additional acid (H+) produced as a result of the cross-linking reaction and hydrolysis, i.e., to keep the pH high enough to achieve the desired gelation time.

It has been discovered, through bench testing, that when cross-linking the SunBio PEG with albumin (Plasbumin), a range of gelation times between an acceptable moderate time (about 30 seconds) to a rapid time (about 2 seconds) can be achieved by establishing a pH range from about 8 (the moderate times) to about 10 (the rapid times). Ascertaining the cross-linking pH range aids in the selection of buffer materials having pK's that can provide the requisite buffering capacity within the pH range.

Phosphate, tris-hydroxymethylaminomethane (Tris), and carbonate are all non-toxic, biocompatible buffers, thereby meeting criteria (1) and (2). Phosphate has a pK of about 7, which provides increased buffering capacity to albumin at pH's up to about 8.5. Tris has a pK of about 8, which provides increased buffering capacity to albumin at pH's up to about 9.5. Addition of Tris to albumin (Plasbumin) at a concentration of 60 mM approximately doubles the buffering capacity of the albumin at a pH near 9. Carbonate has a pK of about 10, and provides increased buffering capacity to albumin in the higher pH ranges. Depending upon the gellation time that is targeted, formulations of Tris, carbonate, and albumin can be used for the buffer material.

EXAMPLE

Carbonate Buffer/Tris Buffer Formulations

Albumin (Human 25%, Plasbumin®-25 manufactured by Bayer Corporation) was buffered using Sodium Carbonate Anhydrous ($Na_2CO_3$) (FW 106.0) ("Carbonate Buffer") mixed with Tris-hydroxymethylaminomethane ($C_4H_{11}NO_3$) (FW 121.1) ("Tris Buffer"). The buffered albumin formulations (2 cc) were mixed with 2 cc of the SunBio PEG (0.45 g of PEG suspended in 2.2 cc of water), to provide 17% w/w PEG solids. The components were mixed in the manner described in Example 1. The pH of the buffered albumin formulation (albumin plus buffer material) and the gelation time (as described above) and were recorded.

Table 1 summarizes the results:

TABLE 1

| Albumin (Human 25%)(ml) | Carbonate Buffer (grams) | Tris Buffer (grams) | pH | Device (Outside Diameter) | Gelling Time (Seconds) |
|---|---|---|---|---|---|
| 20 | 0 | 0.217 | 8.3 | 7 Fr | 11 |
| 20 | 0 | 0.290 | 8.5 | 7 Fr | 7–8 |
| 20 | 0.075 | 0.145 | 8.7 | 7 Fr | 5–6 |
| 20 | 0.138 | 0.145 | 9.0 | 7 Fr | 2–3 |

Table 1 shows rapid gelation times. This is believed due to the larger concentration of multiple functionality PEG in the SunBio PEG, as well as the enhanced buffering capacity that the Tris Buffer (pK 8) provides in the lower pH range (7 to 9). It is also believed that the gelation time will also vary, given the same composition, according to the size and configuration of the delivery device. The addition of Carbonate Buffer (in the pH 8.7 and pH 9 compositions) leads to a further decrease in gelation time, at an increased pH.

Tests of pH 8.3 and pH 8.5 compositions in Table 1 have demonstrated that both composition are successful in sealing femoral puncture sites in sheep in 25 to 40 seconds. The tests also show that either composition possesses sufficient cross-linking capacity to close about the catheter tract following removal of the catheter upwards to two minutes after delivery of the material. Both compositions thereby readily accommodate variations in procedure time.

Tests of pH 8.7 composition in Table 1 have also demonstrated that the composition is successful in sealing femoral puncture sites in sheep in 25 to 40 seconds. The tests also show that, due to the more rapid gelation time, the composition does not possesses sufficient cross-linking capacity to consistently close about the catheter tract following removal of the catheter two minutes after delivery of the material. In this respect, the pH 8.7 composition, despite its faster gelation time, is not as accommodating to changes in procedure time as the pH 8.3 and pH 8.5 compositions, described above. For these reasons, the most preferred range for vessel puncture sealing is between pH 8.3 and pH 8.5.

Further details of the material composition are found in copending U.S. patent application Ser. No. 09/780,014, filed Feb. 9, 2001, and entitled "Systems, Methods, and Compositions for Achieving Closure of Vascular Puncture Sites.

Representative Embodiment

In a representative embodiment employed with a 7 FR device, the vial 94 contains 600 mg±10% of lyophilized SunBio PEG-SG (4-arm polyethylene glycol tetrasuccinimidyl glutarate—MW 10,500±1500). The lyophilization process will be described in detail later. The syringe 98 contains 6 ml of water and 2 ml of buffered 25% w/w human serum albumin, USP. The buffered 25% albumin is made by adding 0.217 g. of Tris-hydroxymethlaminomethane ($C_4H_{11}NO_3$) (FW 121.1) (TRIS Buffer) to 20 cc of Bayer Plasbumin®-25 to obtain a pH between 8.0 and 8.7, most preferably between 8.3 and 8.5. This composition is described in Table 1.

The Lyophilization Process

The PEG material is moisture sensitive, i.e., it can be subject to rapid degradation upon exposure to moisture. This moisture sensitivity can limit the stability of the PEG material and thus its long-term storage or "shelf life." Therefore, as previously noted, it may be desirable that the PEG material be lyophilized and stored under vacuum or inert gas. During lyophilization, a solid substance is isolated from solution by freezing the solution and evaporating the ice under vacuum. The process removes essentially all moisture from the solid substance. By removing essentially all moisture from the PEG, the shelf life can be significantly extended.

A representative lyophilization procedure employing a Stokes Lyophilizer follows:

Sterilize Lyophilizer

In preparing lyophilizer, clean the chamber before use. The sterilization cycle can be run, if needed, to clean the chamber. Before sterilizing chamber, inspect for broken glass, stoppers, residual spilled product, and tape. Clean chamber shelves with alcohol. Check and replace vacuum pump oil as required.

2. Pre-freeze lyophilizer at least 120 minutes before loading the vials into the lyophilizer.

3. Fill vials with 4 ml polymer solution (10% to 20% w/w solution, most desirably 15% w/w solution, PEG-SG in aqueous solution (sterile water)).

4. Place vials in trays into the lyophilizer.

5. Complete lyophilization according to the following table, to yield, in each vial 600 mg±10% of lyophilized PEG-SG material.

Pre-Freeze

| Segment Number | Segment Description | Temperature | Time | Vacuum (mTorr) | Ramp/Soak |
|---|---|---|---|---|---|
| 1 | Loading | −50° C. | 1 minute | Off | Ramp |
| 2 | Pre-freeze | −50° C. | Max. time | Off | Soak |
| 3 | Pre-freeze | −50° C. | 60 minutes | Off | Ramp |
| 4 | Pre-freeze | −40° C. | 10 minutes | 50 | Ramp |

Primary Dry

| Segment Number | Segment Description | Temperature | Time | Vacuum (mTorr) | Ramp/ Soak |
|---|---|---|---|---|---|
| 1 | Primary Drying | +10° C. | 1200 minutes | 50 | Ramp |
| 2 | Primary Drying | +20° C. | 1200 minutes | 50 | Ramp |
| 3 | Primary Drying | +20° C. | 1920 minutes | 50 | Soak |

Cycle End

| Segment Description | Temperature | Time | Ramp/Soak |
|---|---|---|---|
| $N_2$ Backfill | +20° C. | 30 min. to 14.7 PSIA | Soak |
| Stoppering | +20° C. | N/A | N/A |

In use, the 600 mg±10% lyophilized PEG-SG material in each vial is reconstituted with 2 ml buffered human serum albumin (25%) and 6 ml water.

Representative Use of the System to Deliver Material Compositions to Close Vascular Puncture Sites The Introduction Stage (The Composition Liquid Phase)

In the first stage (see FIG. 19), the physician primes the selected catheter assembly 20 and selected introducer/mixing assembly 22 with sterile water or saline. The physician then introduces the selected catheter assembly 20 through the tissue track 34 partially into the blood vessel through the vascular puncture 36. As FIG. 19 shows, the structure 64 is in a collapsed condition at this stage.

Typically, the catheter assembly 20 is introduced along a guide wire 32. As earlier explained and as shown in preceding FIGS. 17 and 18, the guide wire 32 will have been previously introduced percutaneously, through a wall of the blood vessel, to guide passage of a desired therapeutic or diagnostic instrument 30 into the blood vessel. As also previously explained, the diameter of the outer catheter body 26 of the catheter assembly 20 is preferably sized to seal, but not enlarge, the tissue track 34. In other words, the outside diameter of the outer catheter body 26 substantially matches the outside diameter of the vascular introducer 28 (by now retracted).

As FIG. 20 shows, the structure 64 is expanded within the blood vessel (as previously described). The physician applies back pressure on the catheter assembly 20, bringing the expanded structure 64 into contact with the interior of the vessel wall. By gauging the back pressure, the physician locates the nozzles 60 outside the puncture site 36, as FIG. 20 shows. The physician links the formative component assembly 18 through the introducer/mixer assembly 22 to the catheter assembly 20 (as shown in FIG. 13).

Operation of the formative component assembly 18, as previously described, expresses the components 96 and 100, while in liquid form, through the mixer 88 and down the catheter assembly 20 toward the nozzles 60. The gelating components 138 flow out the nozzles 60 and into the subcutaneous tissue surrounding the vessel, as FIG. 21 shows. The catheter assembly 20, which is sized to seal the tissue track 34, blocks substantial flow in a path up the tissue track 34. Thus, the gelating components 138 are directed in a flow radially away from the axis of the catheter assembly 20 and along the axis of the vessel, as FIG. 21 shows.

In FIG. 21, the nozzles 60 are arranged in a circumferentially spaced array, as shown in FIG. 7A. The array is desirably close to the puncture site 36. If the blood vessel has be accessed before in the same region, scar tissue may be present adjacent to the puncture site 36, and the nozzles 60, arranged as shown in FIG. 7A, may reside in the scar tissue region. The scar tissue could interfere with the passage of the gelating components 138. In this circumstance, it may be desirable to arrange the nozzles 60 in the superior-inferior pattern shown in FIG. 7B, in which another array of superior nozzles 60B (located free of the scar tissue region) are axially spaced away from the array of inferior nozzles 60A (located within the scar tissue region). In this arrangement, it is desirable to size the superior nozzles 60B smaller than the inferior nozzles 60A. For example, the superior nozzles 60B can have an outside diameter of about 0.020 inches, whereas the inferior nozzles 60A can have an outside diameter of about 0.035 inches. The differential sizing of the nozzles 60A and 60B creates differential flow, creating a preferred normal flow path (of least flow resistance) through the inferior nozzles 60A, but allowing alternative flow through the superior nozzles 60B should increased flow resistance be encountered through the inferior nozzles 60A due to surrounding tissue morphology.

The spacing between the nozzles 60A and 60B can also vary. For example, the inferior nozzles 60A can be spaced from the structure 64 by 3 to 10 mm, whereas the superior nozzles 60B can be further spaced 5 to 15 mm from the structure 64.

The size of the catheter assembly 20 is selected according to the outside diameter of the introducer sheath 28 used during the preceding therapeutic or diagnostic procedure, during which the arteriotomy was made. For example, a 6 Fr introducer sheath 28 typically has an outside diameter of 7 Fr, so a 7 Fr diameter catheter assembly 20 is selected to seal the arteriotomy after removal of the introducer sheath 28. The gelating composition 138 is delivered in a liquid state adjacent to the arteriotomy, while the catheter assembly 20 prevents the liquid from filling the tissue track 34. This feature ensures that the material composition remains at the arteriotomy for maximum efficacy.

The incoming flow, directed in this manner, creates a tissue space about the puncture site 36 along the axis of the vessel. The gelating components 138 fill this space.

In the gelation process, the electrophilic component and the nucleophilic component cross-link, and the developing composition 138 gains cohesive strength to close the puncture site 36. The electrophilic component also begins to cross-link with nucleophilic groups on the surrounding tissue mass. Adhesive strength forms, which begins to adhere the developing composition to the surrounding tissue mass.

During the introduction stage, before internal cohesive and tissue adhesive strengths fully develop, a portion of the gelating components 138 can enter the blood vessel through the puncture site 36. Upon entering the blood stream, the gelating components 138 will immediately experience physical dilution. The dilution expands the distance between the electrophilic component and the nucleophilic component, making cross-linking difficult. In addition, the diluted components now experience an environment having a pH (7.3 to 7.4) lower than the an effective reactive pH for cross-linking (which is above 8) (as an example, a typical gelation time at pH 8.3 is about 15 to 20 seconds, whereas a typical gelation time at pH 7.4 is over 10 minutes). As a result, incidence of cross-linking within the blood vessel, to form the hydrogel composition, is only a fraction of what it is outside the vessel, where gelation continues.

Furthermore, the diluted electrophilic component will absorb nucleophilic proteins present in the blood. This reaction further reduces the reactivity of the electrophilic component. In blood, the diluted electrophilic component is transformed into a biocompatible, non-reactive entity, which can be readily cleared by the kidneys and excreted. The diluted nucleophilic component 100 is a naturally occurring protein that is handled in normal ways by the body.

The Introduction Stage (The Composition Liquid Phase) preferably last about 5 to 30 seconds from the time the physician begins to mix the components 96 and 100.

The Localized Compression Stage (The Semi-Solid Composition Phase)

The second stage begins after the physician has delivered the entire prescribed volume of components 96 and 100 to the tissue mass of the vessel puncture site 36 and allowed the cross-linking of the components 96 and 100 to progress to the point where a semi-solid gel occupies the formed tissue space.

Figure 22:
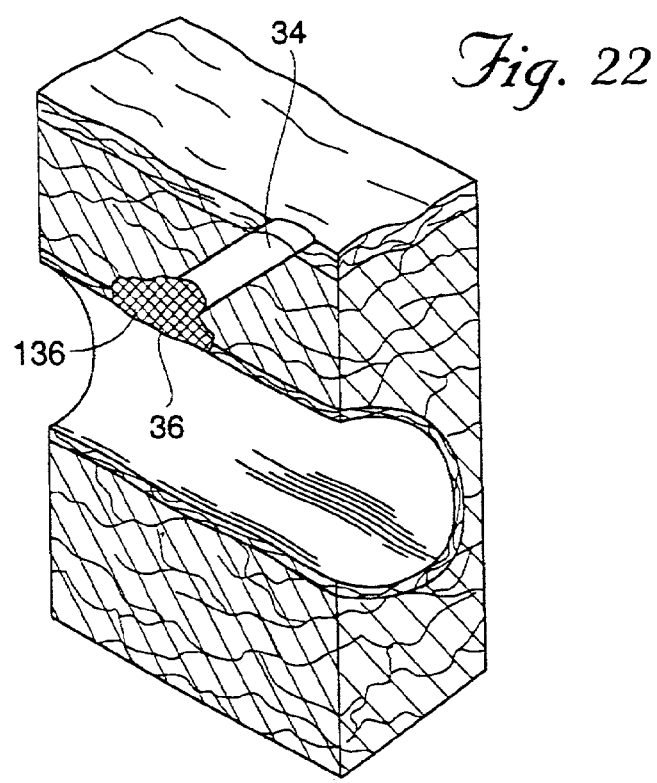
FIG. 22 is a diagrammatic view of the blood vessel puncture site shown in FIG. 21, after removal of the vascular puncture site access assembly and after the closure composition has formed a barrier to seal the puncture site.

At this point (as FIG. 22 shows), the physician collapses the structure 64 and withdraws the catheter assembly 20 and guide wire 32 from the tissue track 34. The physician now simultaneously applies localized and temporary compression to the exterior skin surface surrounding the tissue track 34.

The application of localized pressure serves two purposes. It is not to prevent blood flow through the tissue track 34, as cross-linking of the components 96 and 100 has already proceeded to create a semi-solid gel having sufficient cohesive and adhesive strength to impede blood flow from the puncture site. Rather, the localized pressure serves to compress the tissue mass about the semi-solid gel mass. This compression brings the semi-solid gel mass into intimate contact with surrounding tissue mass, while the final stages of cross-linking and gelation take place.

Under localized compression pressure, any remnant catheter track existing through the gel mass will also be closed.

Under localized compression pressure, surface contact between the adhesive gel mass and tissue is also increased, to promote the cross-linking reaction with nucleophilic groups in the surrounding tissue mass. Adhesive strength between the gel mass and tissue is thereby allowed to fully develop, to firmly adhere the gel mass to the surrounding tissue as the solid composition 136 forms in situ.

During this stage, blood will also contact the vessel-side, exposed portion of the gel mass, which now covers the tissue puncture site. The electrophilic component will absorb nucleophilic proteins present in the blood, forming a biocompatible surface on the inside of the vessel.

The Localized Compression Stage (The Composition Semi-Solid (Gel) Phase) preferably last about 3 to 10 minutes from the time the physician withdraws the catheter assembly 20.

The Hemostasis Stage (The Composition Solid Stage)

At the end of the Localized Compression Stage, the solid composition 136 has formed (as FIG. 22 shows). Hemostasis has been achieved. The individual is free to ambulate and quickly return to normal day-to-day functions.

The mechanical properties of the solid composition 136 are such to form a mechanical barrier. The composition 136 is well tolerated by the body, without invoking a severe foreign body response.

The mechanical properties of the hydrogel are controlled, in part, by the number of crosslinks in the hydrogel network as well as the distance between crosslinks. Both the number of crosslinks and the distance between crosslinks are dependent on the functionality, concentration, and molecular weight of the polymer and the protein.

Functionality, or the number of reactive groups per molecule, affects the mechanical properties of the resulting hydrogel by influencing both the number of and distance between crosslinks. As discussed previously, the utility of a given polymer significantly increases when the functionality is increased to be greater than or equal to three. The observed incremental increase in functionality occurs when the functionality is increased from two to three, and again when the functionality is increased from three to four. By increasing the functionality of the polymer or protein at a constant concentration, the concentration of crosslinking groups available for reaction are increased and more crosslinks are formed. However, increased mechanical properties cannot be controlled with functionality alone. Ultimately, the steric hindrances of the protein or polymer to which the reactive groups are attached predominate and further changes in the mechanical properties of the hydrogel are not observed. The effect of functionality is saturated when the functionality reaches about four.

The concentration of the protein and polymer also affect the mechanical properties of the resulting hydrogel by influencing both the number of and distance between crosslinks. Increasing the protein and polymer concentration increases the number of available crosslinking groups, thereby increasing the strength of the hydrogel. However, decreases in the elasticity of the hydrogel are observed as the concentration of the protein and polymer is increased. The effects on the mechanical properties by concentration are limited by the solubility of the protein and polymer.

The polymer and protein molecular weight affects the mechanical properties of the resulting hydrogel by influencing both the number of and distance between crosslinks. Increasing the molecular weight of the protein and polymer decreases the number of available crosslinking groups, thereby decreasing the strength of the hydrogel. However, increases in the elasticity of the hydrogel are observed with increasing molecular weight of the protein and polymer. Low molecular weight proteins and polymers result in hydrogels that are strong, but brittle. Higher molecular weight proteins and polymers result in weaker, but more elastic gels. The effects on the mechanical properties by molecular weight are limited by the solubility of the protein and polymer. However, consideration to the ability of the body to eliminate the polymer should be made, as large molecular weight polymers are difficult to clear.

The Degradation Stage (The Composition Re-Absorption Phase)

Over a controlled period, the material composition is degraded by physiological mechanisms. Histological studies have shown a foreign body response consistent with a biodegradable material, such as VICRYL™ sutures. As the material is degraded, the tissue returns to a quiescent state. The molecules of the degraded genus hydrogel composition are cleared from the bloodstream by the kidneys and eliminated from the body in the urine. In a preferred embodiment of the invention, the material loses its physical strength during the first fifteen days, and totally resorbs in about four to eight weeks, depending upon the person's body mass.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An assembly comprising
a biocompatible polymer in lyophilized form,
a first container holding the polymer in lyophilized form, the first container including a fluid receiving end,
a protein solution,
a second container holding the protein solution including a fluid dispensing end and a single actuator for expelling the protein solution from the fluid dispensing end, and
applicator to join the fluid receiving end of the first container with the fluid dispensing end of the second container to introduce the protein solution into the first container for mixing with the polymer in lyophilized form to reconstitute the polymer and form a mixture, wherein, upon mixing, the protein solution and the polymer cross-link, the applicator including a first fluid passage adapted to join the fluid dispensing end of the second container in fluid communication with the fluid receiving end of the first container, the first fluid passage including a distal end region that, when the fluid dispensing end of the second container is joined in fluid communication with the fluid receiving end of the first container, extends into the first container to contact the polymer in lyophilized form, the distal end region including a plurality of holes in a side of the distal end region for uniformly introducing the protein solution into the first container for mixing with the polymer in response to operation of the single actuator, the applicator further including a second fluid passage next to the first fluid passage for conveying the mixture from the first container concurrent with introduction of the protein solution into the first container in response to operation of the single actuator.

* * * * *